(12) United States Patent
Yan et al.

(10) Patent No.: US 9,632,058 B2
(45) Date of Patent: Apr. 25, 2017

(54) NON-INVASIVE GLUCOSE SENSOR

(75) Inventors: Feng Yan, Hong Kong (CN); Helen L. W. Chan, Hong Kong (CN); Hao Tang, Hong Kong (CN)

(73) Assignee: The Hong Kong Polytechnic University, Hong Kong (HK)

( * ) Notice: Subject to any disclaimer, the term of this patent is extended or adjusted under 35 U.S.C. 154(b) by 192 days.

(21) Appl. No.: 13/075,027

(22) Filed: Mar. 29, 2011

(65) Prior Publication Data

US 2012/0247976 A1    Oct. 4, 2012

(51) Int. Cl.
  *G01N 33/50*    (2006.01)
  *G01N 27/327*   (2006.01)
  *G01N 27/414*   (2006.01)

(52) U.S. Cl.
  CPC .................. *G01N 27/4145* (2013.01)

(58) Field of Classification Search
  CPC .................. G01N 27/4145; G01N 27/4146
  USPC ...... 257/253; 205/775.5; 204/403.01, 403.06
  See application file for complete search history.

(56) References Cited

U.S. PATENT DOCUMENTS

| | | | |
|---|---|---|---|
| 7,399,400 B2 * | 7/2008 | Soundarrajan et al. ... | 205/777.5 |
| 7,632,600 B2 * | 12/2009 | Kubo et al. ................. | 429/401 |
| 2007/0077483 A1 | 4/2007 | Kubo et al. | |
| 2009/0040587 A1 * | 2/2009 | Kugler ......................... | 359/265 |

FOREIGN PATENT DOCUMENTS

| | | |
|---|---|---|
| CN | 1563969 A | 1/2005 |
| CN | 101101273 A | 1/2008 |
| CN | 101329296 A | 12/2008 |
| CN | 101393160 A | 3/2009 |
| CN | 101581691 A | 11/2009 |

OTHER PUBLICATIONS

Kang et al., Analytical Biochemistry, 369, Jul. 2007, 71-79.*
Macaya et al., Sensors and Actuators B, 123, Oct. 2006, 374-378.*
Chapter 8 of Materials Science, vol. 107, 2008, "Organic Semiconductors in Sensor Applications", Editors: Dr. Daniel A. Bernards, Professor George G. Malliaras, Dr. Róisín M. Owens.*
Chen et al. (Organic Electronics, 7, 2006, 435-439).*
Kim et al. (Appl. Phys. Lett. 93, 2008, 013302).*
Tang et al. (Advanced Functional Materials, published online Apr. 26, 2011, pp. 2264-2272).*
Berggren et al., "Organic Bioelectronics", Adv. Mater., 2007, vol. 19, pp. 3201-3213.
Bernards et al., "Enzymatic sensing with organic electrochemical transistors", Journal of Materials Chemistry, 2008, vol. 18, pp. 116-120.
Bernards et al., "Steady-State and Transient Behavior of Organic Electrochemical Transistors", Adv. Funct. Mater., 2007, vol. 17, pp. 3538-3544.

(Continued)

*Primary Examiner* — Matthew Martin
*Assistant Examiner* — Steven E Rosenwald
(74) *Attorney, Agent, or Firm* — KPPB LLP

(57) ABSTRACT

A non-invasive glucose sensor (10) for detecting an amount of glucose in bodily fluid, comprising: an organic electrochemical transistor (OECT) having a gate electrode (20); wherein a surface of the gate electrode (20) is modified with an enzyme and a nanomaterial to increase sensitivity and selectivity of the gate electrode (20).

10 Claims, 26 Drawing Sheets

(56) References Cited

OTHER PUBLICATIONS

Cicoira et al., "Influence of Device Geometry on Sensor Characteristics of Planar Organic Electrochemical Transistors", Adv. Mater. 2010, vol. 22, pp. 1012-1016.
Estrela et al., "Field effect detection of bimolecular interactions;", Electrochimica Acta, 2005, vol. 50, pp. 4995-5000.
Khan et al., "In Situ, label-Free DNA Detection Using Organic Transistor Sensors", Advanced Materials, 2010, vol. XX, pp. 1-5.
Lin et al., "Improvement of the Tunable Wettability Property of Poly(3-alkylthiophene) Films", Lanemuir, 2009, vol. 25, No. 13, pp. 7465-7470.
Lin et al., "Ion-Sensitive Properties of Organic Electrochemical Transistors", Applied Materials & Interfaces, 2010, vol. 2, No. 6, pp. 1637-1641.
Mabeck et al., "Chemical and biological sensors based on organic thin-film transistors", Anal. Bioanal. Chem., 2006, vol. 384, pp. 343-353.
Macaya et al., "Simple glucose sensors with micromolar sensitivity based on organic electrochemical transistors", Sensors and Actuators, 2007, vol. B 123, pp. 374-378.
Mishizawa et al., "Penicillin Sensor Based on a Microarray Electrode Coated with pH-Responsive Polypyrrole", Ana. Chem., 1992, vol. 64, pp. 2642-2644.
Mok et al., "Organic phototransistor based on poly(3-hexylthiophene)TiO2 nanoparticle", Applied Physics Letters, 2008, vol. 93, pp. 023310-1-023310-3.
Nilsson et al., "An all-organic sensor-transistor based on a novel electrochemical transducer concept printed electrochemical sensors on paper", Sensors and Actuators, 2002, vol. B 86, pp. 193-197.
Someya et al., "Chemical and Physical Sensing by Organic Field-Effect Transistors and Related Devices", Advanced Materials, 2010, vol. 22, pp. 3799-3811.
Thackeray et al., "Chemically Responsive Microelectrochemical Devices Based on Platinized Poly(3-methylghiophene): Variation in Conductivity with Variation in Hydrogen, Oxygen or pH in Aqueous Solution", J. Phys. chem., 1986, vol. 90, pp. 6674-6679.
White et al., "Chemical Derivatization of an Array of Three Gold Microelectrodes with Polypyrrole: Fabrication of a Molecule-Based Transistor", J. Am. Chem. Soc., 1984, vol. 106, pp. 5375-5377.
Yan et al., "Application of thin-film transistors in label-free DNA biosensors", Expert Rev. Mol. Diagn, 2010, vol. 10, No. 5, pp. 547-549.
Yan et al., "Highly photosensitive thin film transistors based on a composite of poly(3-hexylthiophene) and titania nanoparticles", Journal of Applied Physics, 2009, vol. 106, pp. 074501-1-074501-7.
Yan et al., "Label-free DNA sensor based on organic thin film transistors", Biosensors and Bioelectronics, 2009, vol. 24, pp. 1241-1245.
Zhu et al., "A simple poly(3,4-ethylene dioxythiophene)/poly(styrene Sulfonic acid) transistor for glucose sensing at neutral pH", Chem. Commun., 2004, pp. 1556-1557.

\* cited by examiner

Figure 1
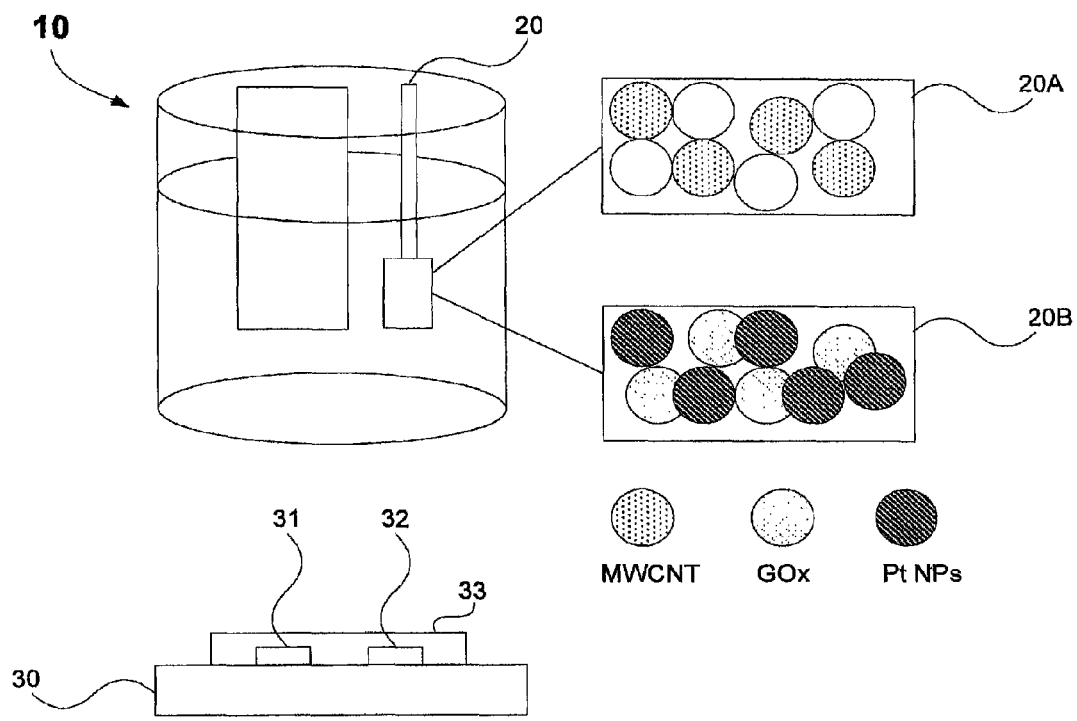
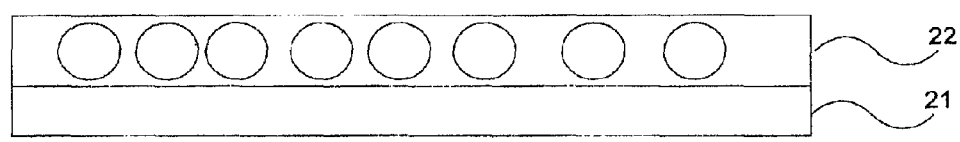
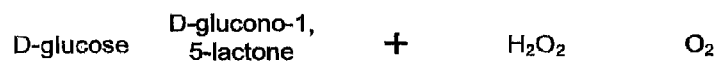

NON-INVASIVE GLUCOSE SENSOR

TECHNICAL FIELD

The invention concerns a non-invasive glucose sensor for detecting glucose level in bodily fluid.

BACKGROUND OF THE INVENTION

Thin film transistors have been regarded as excellent transducers for highly sensitive and disposable biosensors. Sensors based on organic thin film transistors (OTFT) have attracted much attention recently for its easy fabrication and low cost. Organic electrochemical transistors (OECT), are an interesting class of OTFT, and have been extensively studied for the applications of sensors due to their low operating voltages, simplified structure, and the ability to operate in aqueous environments that are essential for biological applications. The first OECT based on polypyrrole was reported in 1984 which was a new direction in the field of OTFTs. Since then, OECTs based on several different conducting polymers were investigated and have shown broad applications of chemical and biological sensing, including humidity sensors, pH and ion sensors, glucose sensors, and cell-based biosensors. The conducting polymer PEDOT:PSS has very important applications in organic electronic devices, including organic solar cells, organic light emission diodes and OTFTs, due to its high conductivity and solution processibility. Recently, PEDOT:PSS has been successfully used as the active layer of OECTs and such devices have shown excellent performance in various applications especially for biosensors in view of their biocompatibility and stability in aqueous environments.

A highly sensitive glucose sensor is desirable in the diagnosis of diabetes. The application of OECTs based on PEDOT:PSS in glucose sensors has been reported. For these sensors, enzyme (glucose oxidase) and glucose are mixed together in aqueous solutions during the measurement without any surface modification on the gate and the active layer of the OECTs. The detection limit of that type of glucose sensor is about several μM, which is sensitive enough for measuring glucose levels in human saliva. Therefore the application of these devices is for low cost and noninvasive blood glucose monitoring.

SUMMARY OF THE INVENTION

In a first preferred aspect, there is provided a non-invasive glucose sensor for detecting an amount of glucose in bodily fluid, comprising:
an organic electrochemical transistor (OECT) having a gate electrode;
wherein a surface of the gate electrode is modified with an enzyme and a nanomaterial to increase sensitivity and selectivity of the gate electrode.

The gate electrode may be a Pt gate electrode.

The enzyme may be glucose oxidase (GOx).

The nanomaterial may be any one from the group consisting of: multi-walled carbon nanotubes (MWCNTs) and platinum nanoparticles (Pt-NPs).

The bodily fluid may be any one from the group consisting of: saliva, tissue fluid, sweat and aqueous humor.

The gate electrode may be composed of MWCNT-CHIT/GOx/Pt or CHIT/GOx/Pt-NPs/Pt.

In a second aspect, there is provided a method for manufacturing a non-invasive glucose sensor for detecting an amount of glucose in bodily fluid, the method comprising:

drop coating a glucose oxidase (GOx) Phosphate Buffered Saline (PBS) solution onto a surface of a substrate to form a GOx/Pt electrode; and drop coating a nanomaterial chitosan (CHIT) hybrid aqueous solution onto a surface of the GOx/Pt electrode after the GOx PBS solution has dried on the surface of the substrate.

In a third aspect, there is provided a method for detecting an amount of glucose in bodily fluid, the method comprising:

bio-catalyzing D-glucose by glucose oxidase (GOx) to produce hydrogen peroxide ($H_2O_2$) and D-glucono-1,5-lactone;

electro-oxidizing the produced $H_2O_2$ at a surface of a gate electrode;

wherein the surface of the gate electrode is modified with an enzyme and a nanomaterial.

In a fourth aspect, there is provided a gate electrode for a non-invasive glucose sensor, comprising:
a surface that is modified with an enzyme and a nanomaterial to increase sensitivity and selectivity of the gate electrode.

The present invention provides a new OECT-based glucose sensor by modifying the gate electrode of the OECT with an enzyme and nanomaterials. The enzyme is glucose oxidase (GOx) and the nanomaterials include carbon nanotubes (CNTs) or platinum nanoparticles (Pt-NPs). Such a sensor shows a significant improvement in the device performance. Furthermore, it is not necessary to add enzyme in the glucose solution as required in the prior art when such sensor is used, which will be more convenient for actual use.

CNTs have been widely used for many types of sensors. CNTs are of great interest for ensembles of nanostructural electrodes for biosensors and nano-bioelectronics because of their nanometer size, good electrocatalytic property and capacity for biomolecule immobilization. Pt-NPs are very effective as a matrix for enzyme immobilization due to good biocompatibility and huge surface area. Pt-NPs improve the immobilization efficiency and maintain the bioactivity of GOx and therefore significantly enhance the sensitivity of the sensor. Moreover, Pt-NPs possess excellent electrocatalytic activity to hydrogen peroxide ($H_2O_2$), which is critical to the glucose sensors based on the detection of $H_2O_2$. Another important material for the modification of the enzyme electrode is chitosan (CHIT), which is a biocompatible polymeric matrix. CHIT displays good film-forming ability, high water permeability and susceptibility to chemical modifications, which can noncovalently associate with CNTs to form a biocompatible nanotube hybrid aqueous suspension. The integration of CNTs or Pt-NPs with CHIT has been used to improve the performance of the OECT-based glucose biosensors.

In the present invention, multi-walled carbon nanotubes (MWCNTs)-CHIT hybrid and electro-deposited Pt-NPs are used to modify the surface of the Pt electrodes before the immobilization of GOx. Then, the MWCNT-CHIT/GOx/Pt and CHIT/GOx/Pt-NPs/Pt electrodes are used as the gate electrodes of the PEDOT:PSS-based OECTs. Advantageously, the sensitivity of the devices can be greatly improved by using these gate electrodes, and the detection limit is extended by more than three orders of magnitude compared to prior art gate electrodes.

BRIEF DESCRIPTION OF THE DRAWINGS

An example of the invention will now be described with reference to the accompanying drawings, in which FIG. 1 is a schematic diagram of the device structure of PEDOT:PSS-based OECT glucose sensor (top) and the bio-catalyzed reaction cycle involved in the determination of glucose by PEDOT:PSS-based OECTs (below);

DETAILED DESCRIPTION OF THE DRAWINGS

Figure 2:
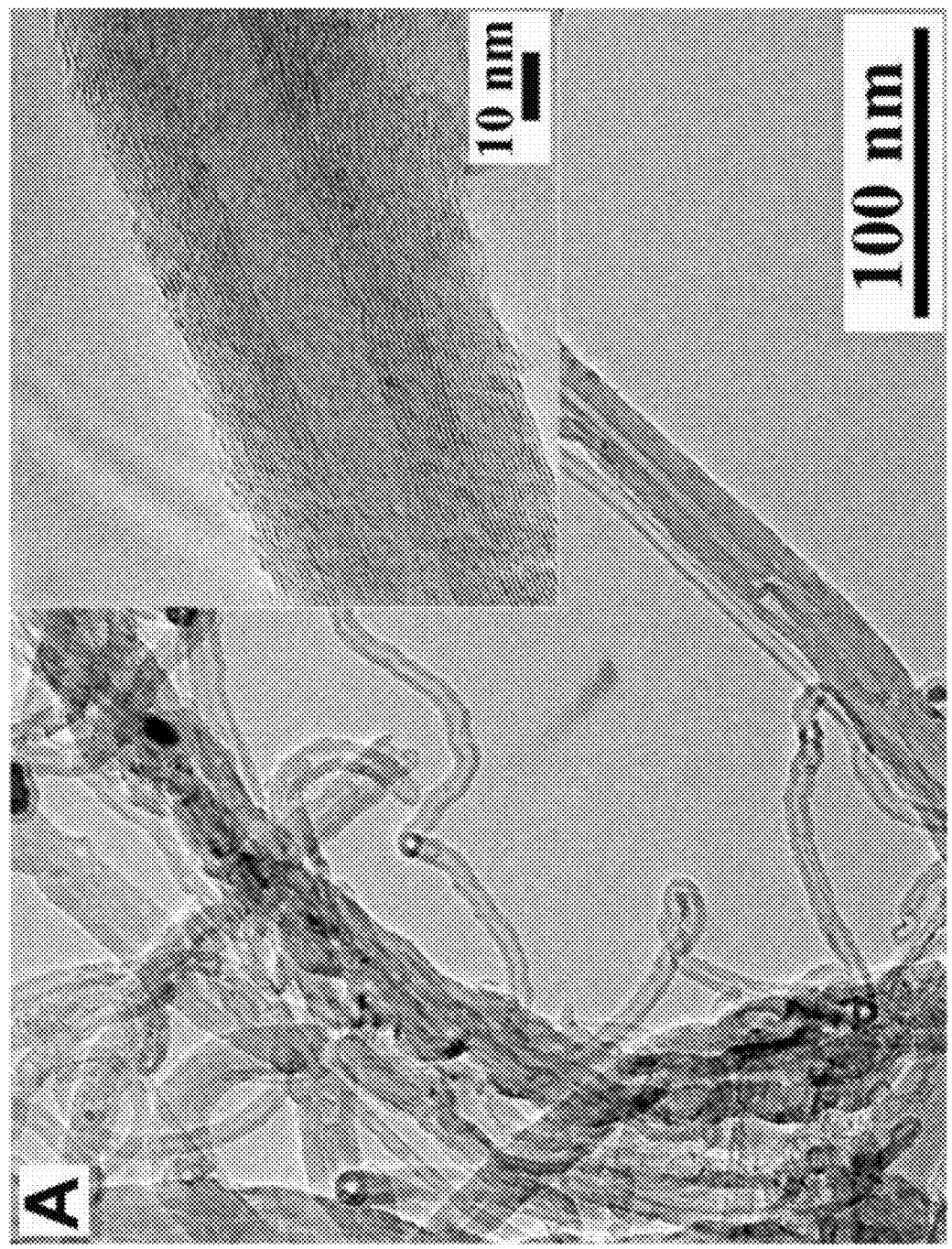
FIG. 2 is a TEM image of MWCNTs.
Figure 3:
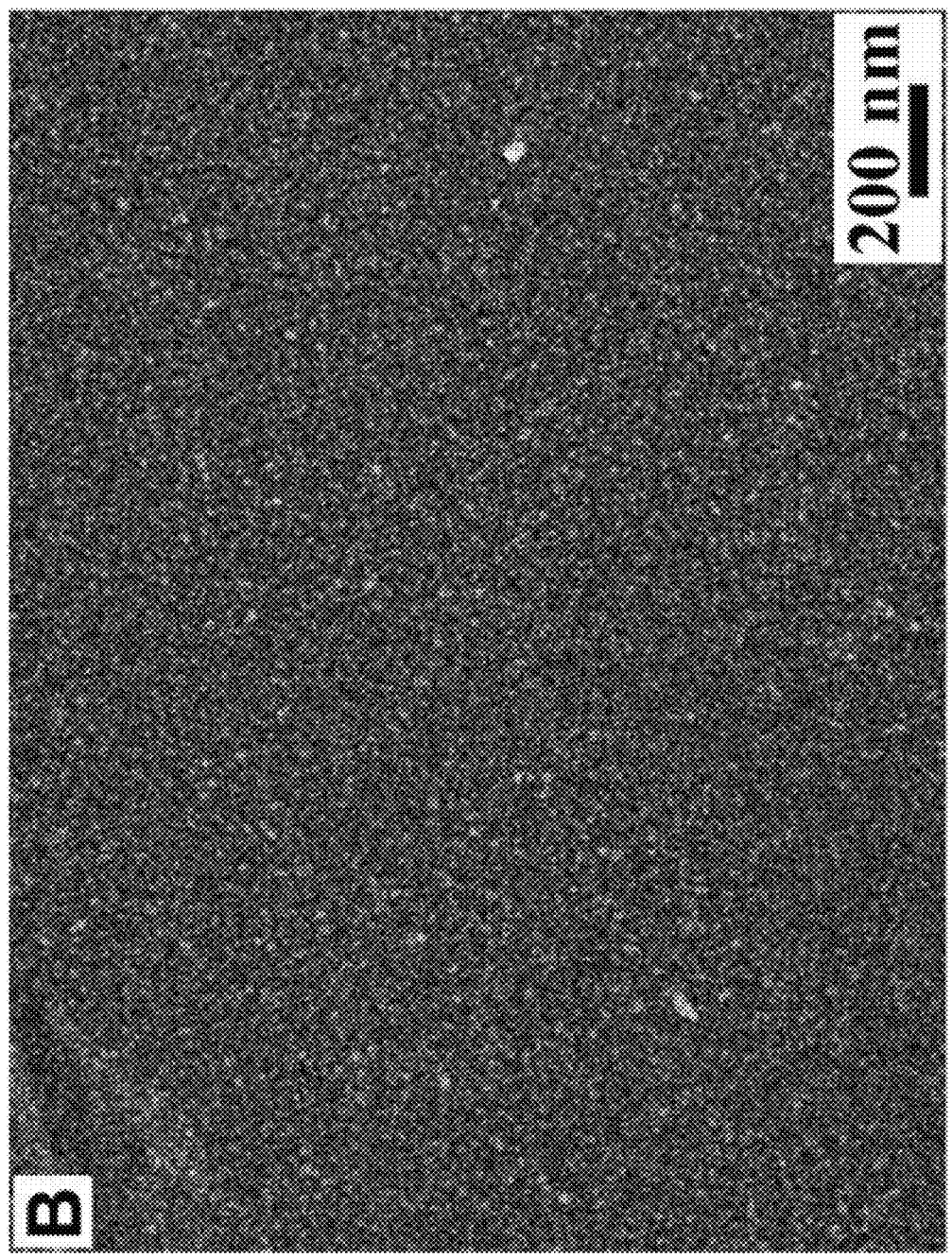
FIG. 3 is a TEM image of Scanning Electron Microscope (SEM) images of Pt substrate.

Referring to FIG. 1, a organic electrochemical transistor (OECT) based glucose sensor 10 with an active layer of PEDOT:PSS 33 is provided. Glass slides 30 are used as the substrates for the fabrication of the sensor 10. Patterned Au/Cr source electrodes 31 and drain electrodes 32 are deposited on the surface of glass substrates 30 through a shadow mask by thermal evaporation. A thin layer of Cr with a thickness of ~5 nm is used as an adhesion layer for the Au film with a thickness of ~50 nm. A PEDOT:PSS layer 33 with a thickness of ~80 nm is then spin coated on top of the glass substrate and patterned on the source electrode 31 and drain electrode 32, followed by thermal annealing at 200° C. for one hour in a glovebox filled with high purity $N_2$. The PEDOT:PSS thin film 33 enables the device 10 to be manufactured at low cost. The channel length and width of the OECT device 10 are 0.2 mm and 6 mm, respectively. MWCNT-CHIT/GOx/Pt, CHIT/GOx/Pt-NPs/Pt or CHIT/GOx/Pt electrodes with an apparent surface area of 0.20 cm$^2$ serve as gate electrodes 20 of the OECTs 10.

For the preparation of MWCNT-CHIT/GOx/Pt gate electrodes 20A, a glucose oxidase (GOx) Phosphate Buffered Saline (PBS) solution with a volume of 20 µL is drop coated onto the surface of each Pt substrate 21 with a pipette and dried at 4° C. GOx is only immobilized on the gate electrode 20A. In order to maintain the immobilized GOx molecules and improve the performance of the enzyme electrodes, 10 µL of a MWCNT-CHIT hybrid aqueous suspension is drop coated on the surface of the GOx/Pt electrodes. After the CHIT films 22 are formed, the MWCNT-CHIT/GOx/Pt gate electrodes 20A are rinsed thoroughly with de-ionized water and stored at 4° C. for future use.

For the preparation of CHIT/GOx/Pt-NPs/Pt gate electrodes 20B, Pt-NPs are first electro-deposited on the rinsed Pt substrate 21 in 5 mM $H_2PtCl_6$+0.05 M HCl aqueous solution. The electro-deposition potential is fixed at −0.3 V (Ag/AgCl) and the deposition time is selected at 30, 60, 90, and 120 seconds, respectively. After being rinsed with de-ionized water carefully, the CHIT/GOx/Pt-NPs/Pt gate electrodes 20B are fabricated with the same processes as described above for the MWCNT-CHIT/GOx/Pt gate electrodes 20A. For comparison, the CHIT/GOx/Pt gate electrodes 20B are also prepared by the same procedure described above.

Referring to FIG. 1, the OECT devices 10 are characterized by using a semiconductor parameter analyzer in a small beaker filled with PBS (pH 7.2). A MWCNT-CHIT/GOx/Pt electrode 20A or CHIT/GOx/Pt-NPs/Pt electrode 20B is used as the gate electrode 20. Before measurement, all of the as-prepared gate electrodes 20 are immersed in PBS (pH 7.2) for 15 minutes to remove unwanted residua. The OECT device 10 is tested at a fixed $V_D$=−0.2 V and a constant or variable different gate voltages. The working principle of the glucose determination by PEDOT:PSS-based OECTs is shown in FIG. 1. The added D-glucose is bio-catalyzed by GOx and the reaction produces $H_2O_2$ and D-glucono-1,5-lactone. At the same time the produced $H_2O_2$ is electro-oxidized at the gate electrode 20.

A CHI660B electrochemical workstation is used to characterize the electrochemical properties of the different gate electrodes 20 in stirred PBS (pH 7.2) solutions. In the measurements, a Pt foil and an Ag/AgCl electrode serves as the counter electrode and reference electrode, respectively. All experiments are performed at room temperature. The MWCNT-CHIT/Pt gate electrode 20A and Pt-NPs/Pt gate electrode 20B are investigated by cyclic voltammetry (CV) in PBS (pH 7.2) containing 5 mM $[Fe(CN)_6]^{3-/4-}$ redox probe, which is usually utilized to characterize the surface feature of the electrodes 20A, 20B.

Surface capacitance of the electrodes 20A, 20B in PBS solution is characterized by using an impedance analyzer with a standard three-electrode system at a frequency of 0.1 Hz. The amplitude of the applied ac signal is 50 mV.

Figure 4:
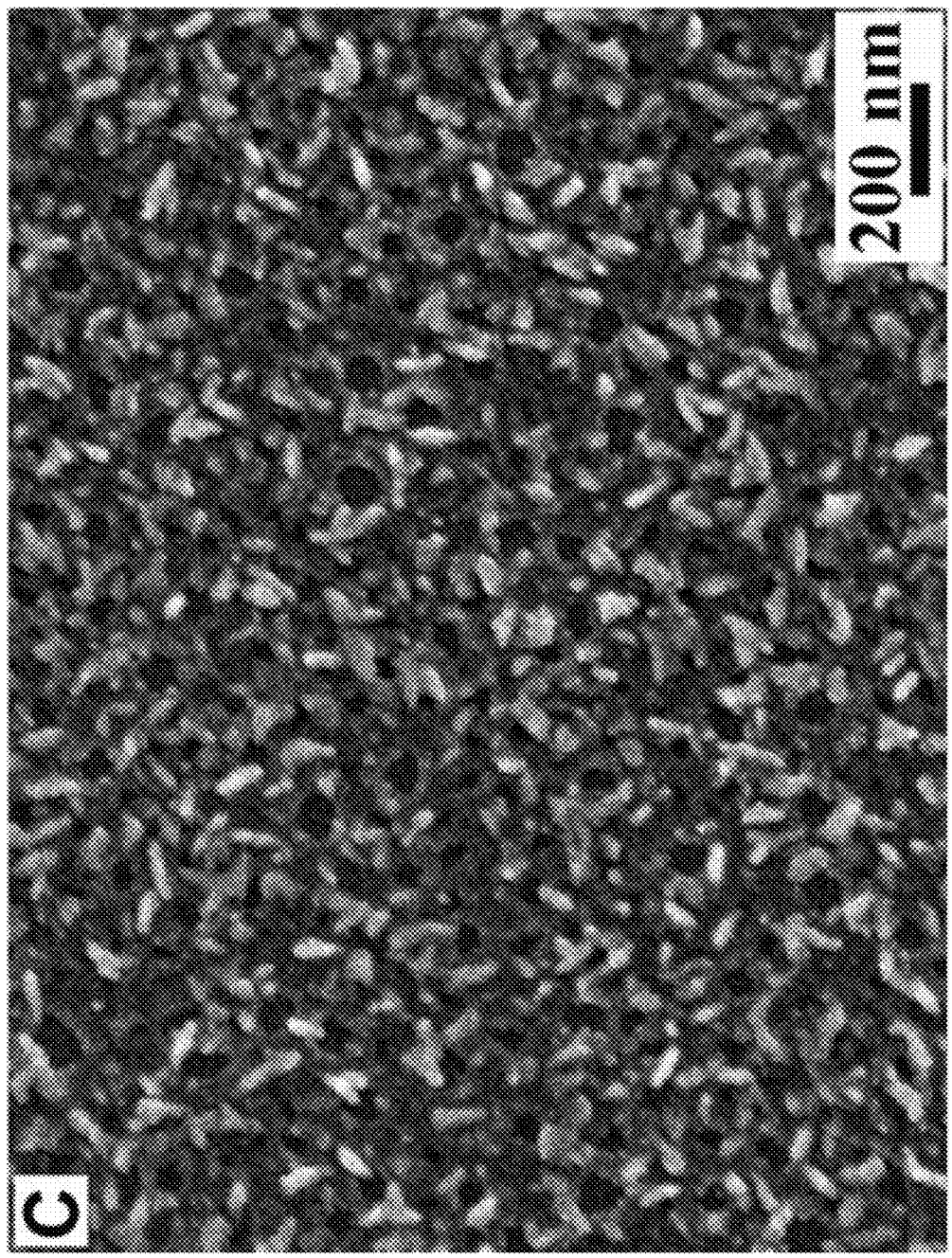
FIG. 4 is a TEM image of Pt-NPs modified Pt electrodes with Electro-deposition time of the Pt-NPs of 30 s.
Figure 5:
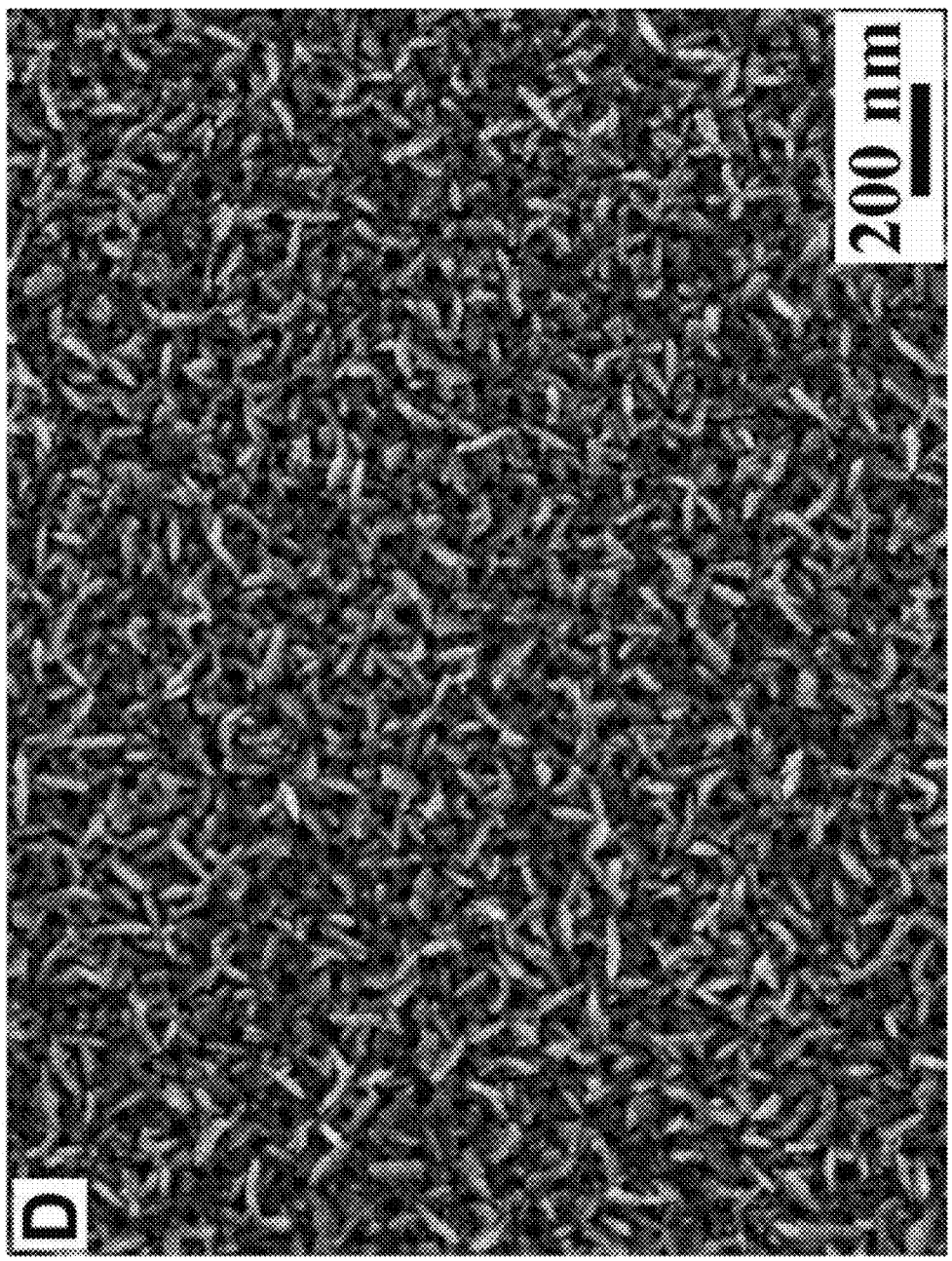
FIG. 5 is a TEM image of Pt-NPs modified Pt electrodes with Electro-deposition time of the Pt-NPs of 60 s.
Figure 6:
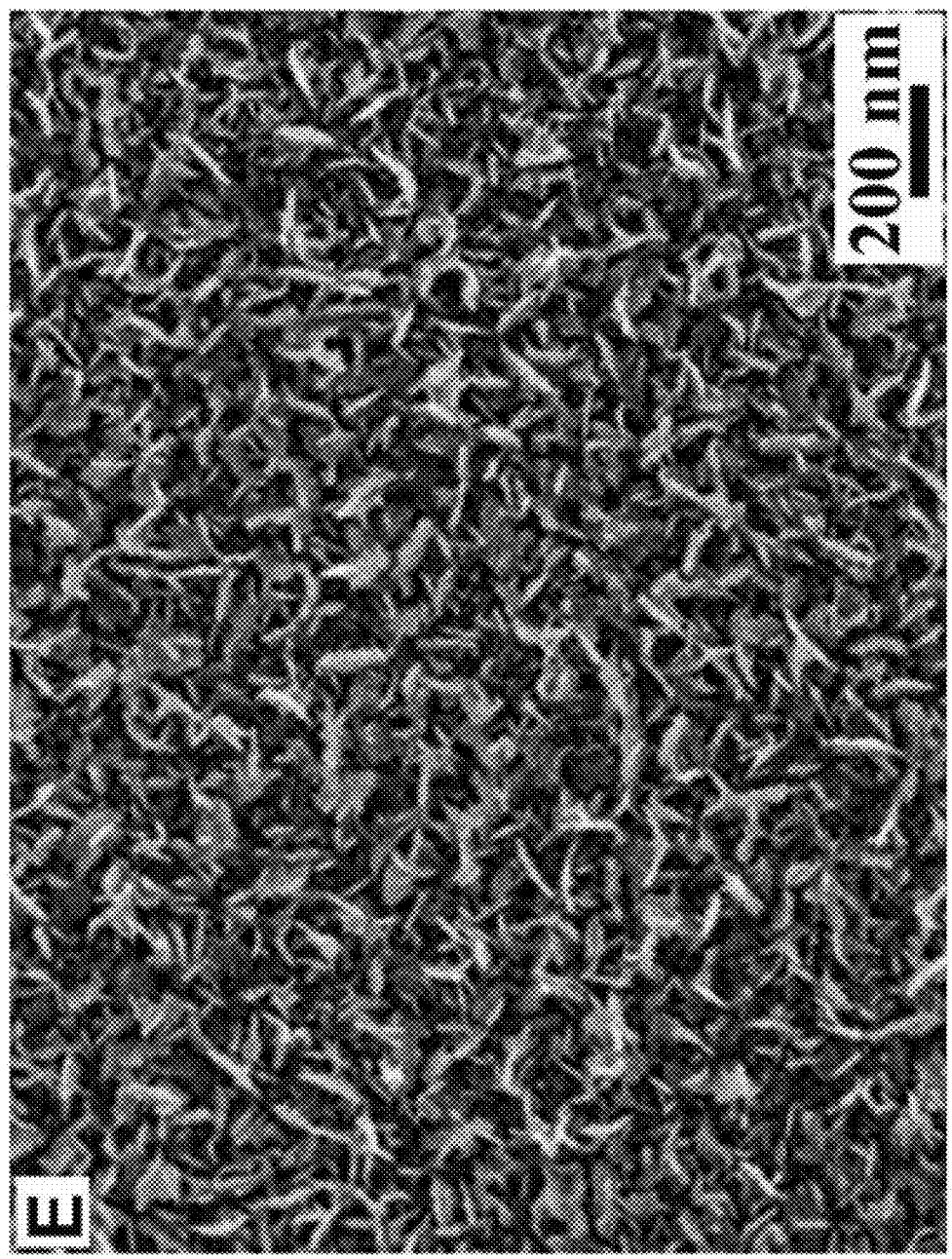
FIG. 6 is a TEM image of Pt-NPs modified Pt electrodes with Electro-deposition time of the Pt-NPs of 90 s.
Figure 7:
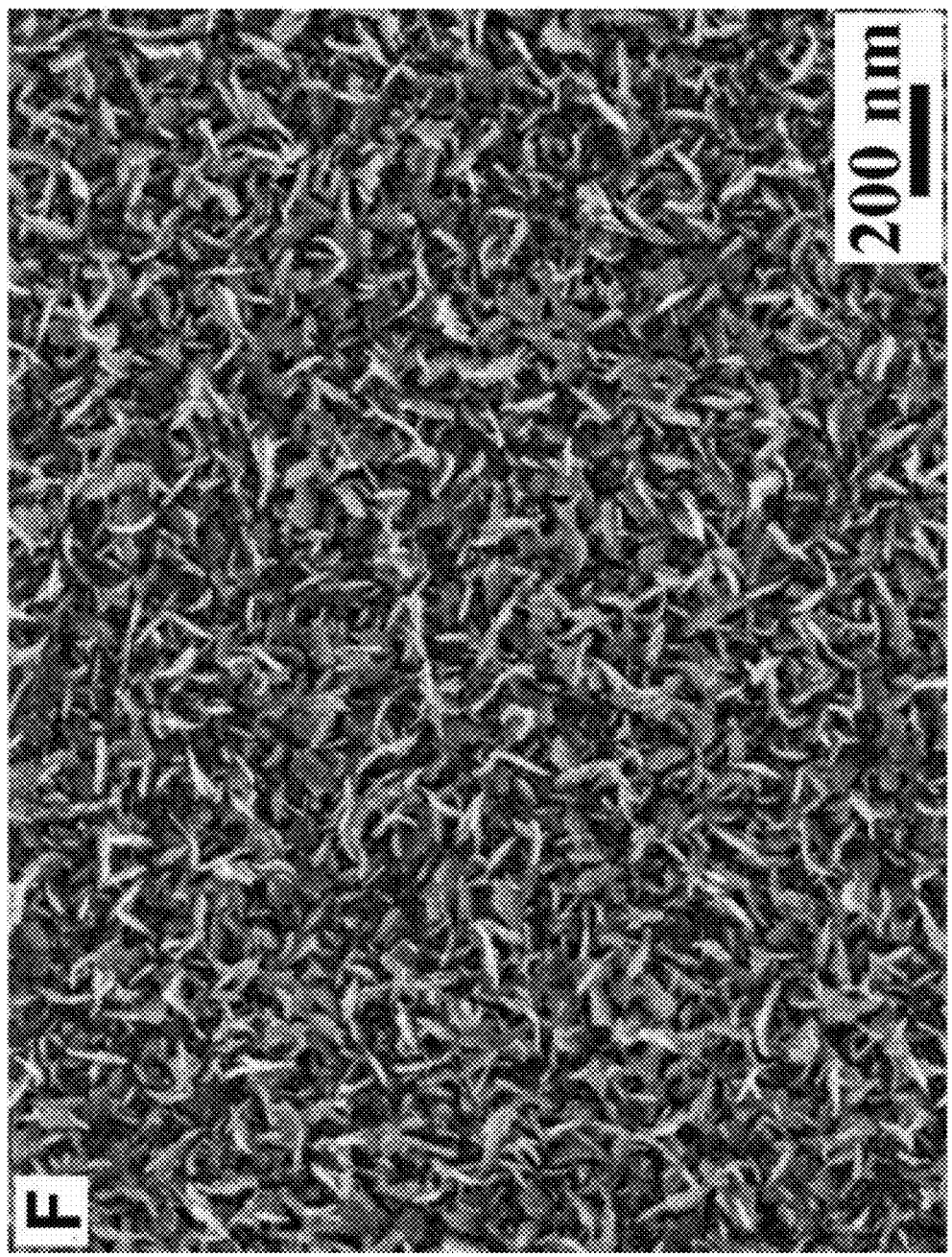
FIG. 7 is a TEM image of Pt-NPs modified Pt electrodes with Electro-deposition time of the Pt-NPs of 120 s.

FIG. 2 shows the morphologies of the MWCNTs and Pt-NPs. The diameter of the MWCNTs is in the range of 10-40 nm. The Pt-NPs are successfully electro-deposited on the surface of Pt substrate with relatively uniform distribution. The average size of the Pt-NPs is about 100 nm (in FIG. 4, deposition time 30 s). With a prolonged deposition time of 60 s, the size of the Pt-NPs has no obvious change but the density of particles increases (in FIG. 4). Further increase of the deposition time results in the Pt-NPs growing up to sheets (in FIGS. 5 to 7).

Figure 8:
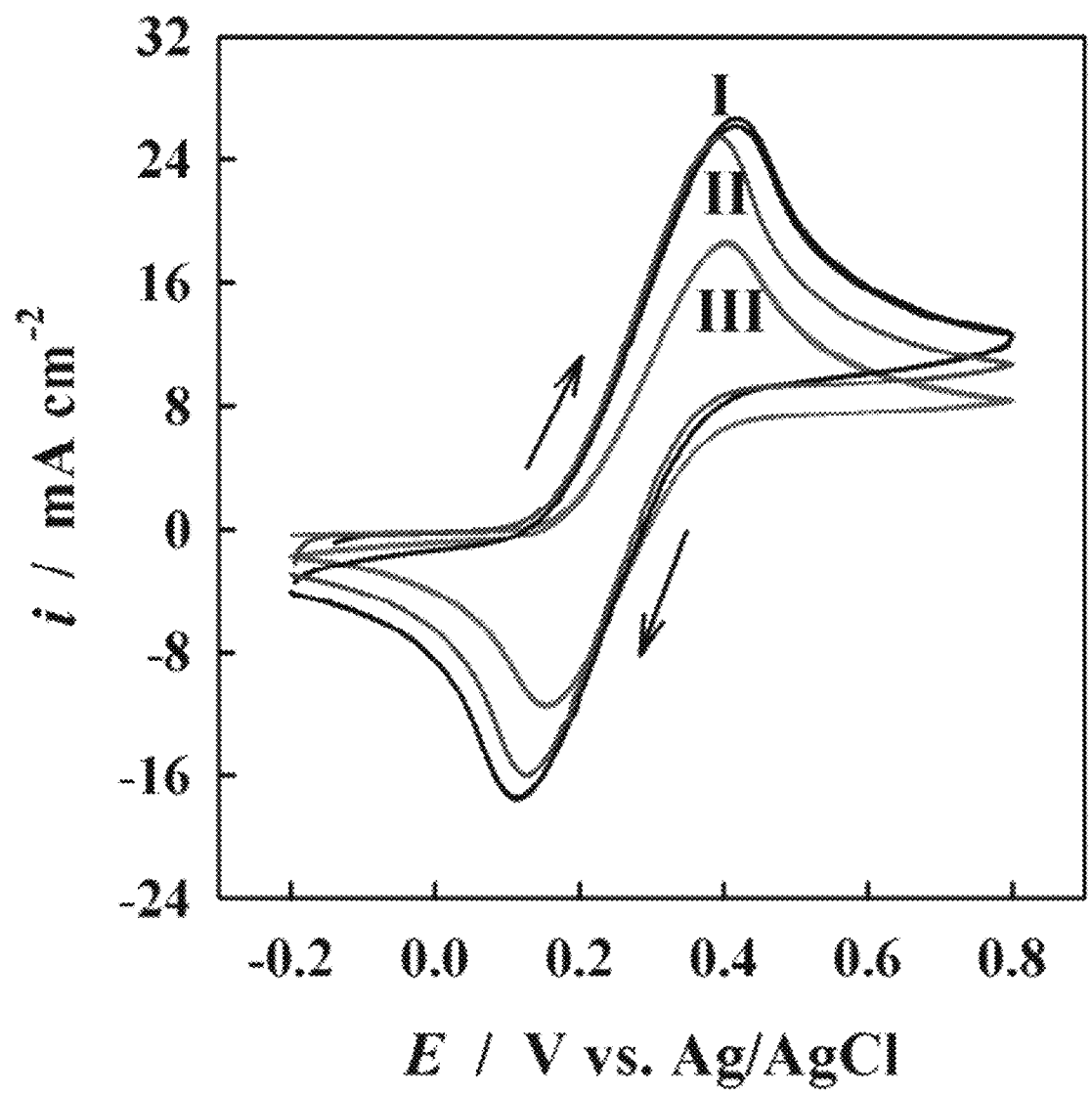
FIG. 8 is a chart depicting the cyclic voltammograms of MWCNT-CHIT/Pt (I), Pt-NPs/Pt (II) and Pt (III) electrodes measured in PBS (pH 7.2) solutions containing 5 mM $[Fe(CN)_6]^{3-/4-}$ redox probe and the CV scan rate is 50 mV s$^{-1}$, and the deposition time of Pt-NPs is 60 s.
Figure 9:
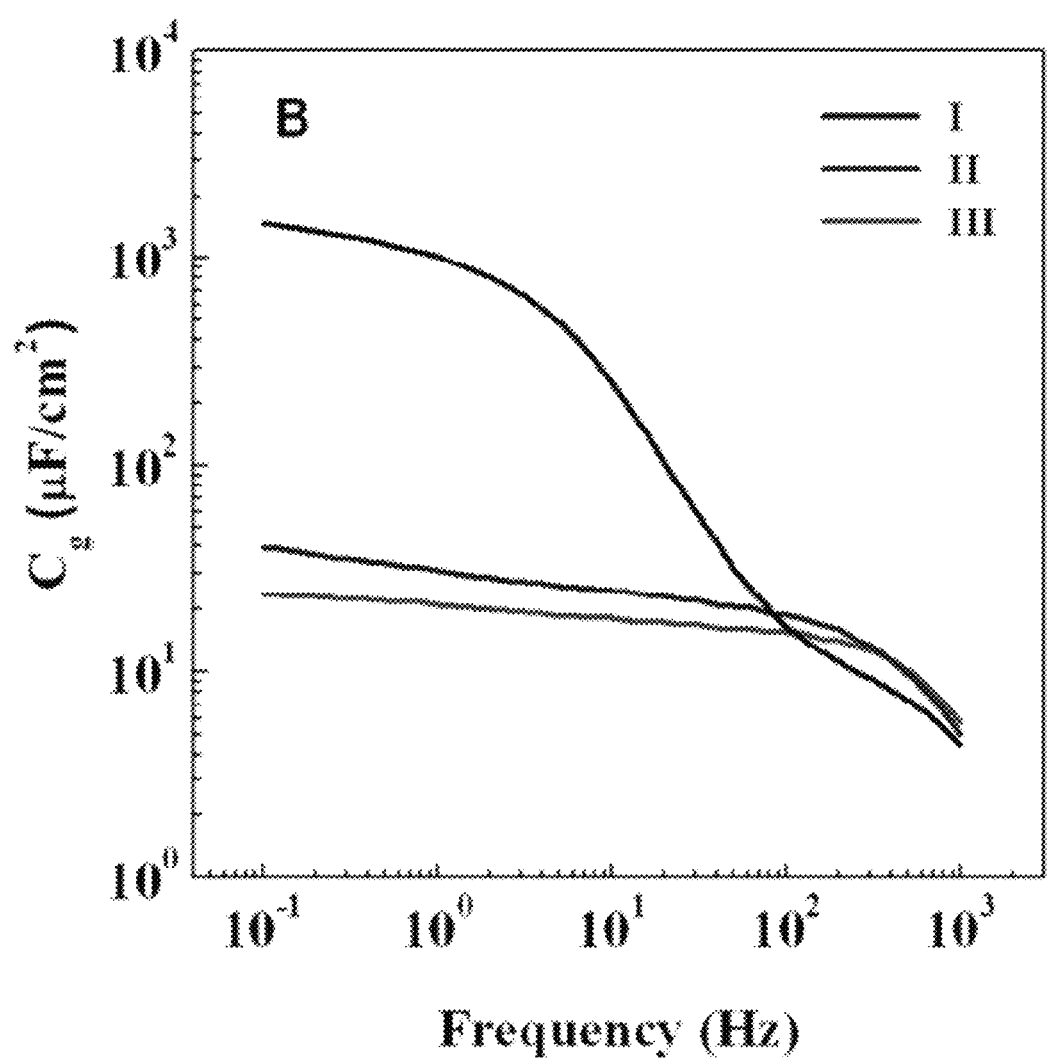
FIG. 9 is a chart depicting surface capacitances of the three electrodes characterized in PBS solution at different frequencies where the area of every electrode is 0.25 cm$^2$.

FIG. 8 shows the electrochemical performance of the MWCNT-CHIT/Pt gate electrode 20A (line I), Pt-NPs/Pt gate electrode 20B (line II) and Pt gate electrode (line III) with the same size. The first two gate electrodes 20A, 20B have very similar redox current densities while the third gate electrode shows a lower value, indicating that the MWCNT-CHIT/Pt gate electrode 20A and Pt-NPs/Pt gate electrode 20B have a larger active surface area than a flat Pt electrode. FIG. 9 shows the capacitances of these three electrodes characterized in PBS solution at zero bias voltage. Since the capacitances at low frequencies (<1 Hz) are approximately proportional to the surface areas of the electrodes, the Pt-NPs/Pt gate electrode 20B has a surface area of about two times of its geometric size while the MWCNT-CHIT/Pt gate electrode 20A has a surface area about 50 times of the geometric size.

The channel current $I_{DS}$ of an OECT 10 as a function of gate voltage $V_G$ is given by the following equation:

$$I_{DS} = \frac{q\mu p_0 t W}{L V_p}\left(V_p - V_g^{eff} + \frac{V_{DS}}{2}\right)V_{DS}, \quad \text{Equation (1)}$$

$$(\text{when}\, |V_{DS}| << |V_p - V_g^{eff}|)$$

$$V_p = qp_0 t/c_i,$$

$$V_g^{eff} = V_G + V_{offset},$$

where q is electronic charge, $p_0$ the initial hole density in the organic semiconductor, μ the hole mobility, t the thickness of the active film, $V_p$ the pinch-off voltage, $V_g^{eff}$ the effective gate voltage applied, and $V_{offset}$ an offset voltage at interfaces, W and L are the width and length of the OECT device 10, respectively. $c_i$ is the effective capacitance per unit area of the transistor, which is related to the capacitances of the two interfaces: electrolyte/semiconductor and electrolyte/gate. $c_i$ is approximately equal to the total capacitance of the two interfaces connected in series divided by the area of the channel.

An OECT-based biosensor is sensitive to the potential drop at the interface of electrolyte/semiconductor or electrolyte/gate. For the glucose sensor 10, $H_2O_2$ is generated by the reaction of D-glucose bio-catalyzed by GOx on the Pt gate electrode 20 and the electro-oxidation of $H_2O_2$ can induce a potential drop at the surface of the electrode. In this case, the gate electrode 20 has Faradic current, which corresponds to electron transfer due to the reaction of $H_2O_2$ as shown in FIG. 1. Therefore, the variation of the chemical potential at the electrolyte/gate interface is related to the concentration of $H_2O_2$ and can be normally described with the Nernst equation:

$$\Delta V_{H_2O_2} = \frac{kT}{2q}\ln[H_2O_2],$$

where k is Boltzmann constant, T is temperature and $[H_2O_2]$ is the concentration of $H_2O_2$. The potential drop will modulate the effective gate voltage applied on the OECT device 10, which can be included in the offset voltage $V_{offset}$ in Equation (1). Therefore the effective gate voltage is given by:

$$V_g^{eff} = V_G + (1+\gamma)\frac{kT}{2q}\ln[H_2O_2] + \text{constant} \quad \text{Equation (2)}$$

where γ is the ratio between the capacitances of the two interfaces: electrolyte/PEDOT:PSS and electrolyte/gate. However, as shown in the following experiments, Equation (2) only can be used for flat Pt gate electrodes. For nanomaterial-modified Pt gate electrodes 20, the relationship between the effective gate voltage and the concentration of $H_2O_2$ is more complicated.

To compare the current responses of different devices to glucose, normalized current response is calculated according to the following equation:

$$NCR = \left|\frac{I_D^{conc} - I_D^{conc=0}}{I_D^{conc=0}}\right|, \quad \text{Equation (3)}$$

where $I_D^{conc=0}$ and $I_D^{conc}$ are the channel currents before and after an addition of glucose at the concentration of interest, respectively.

Figure 10:
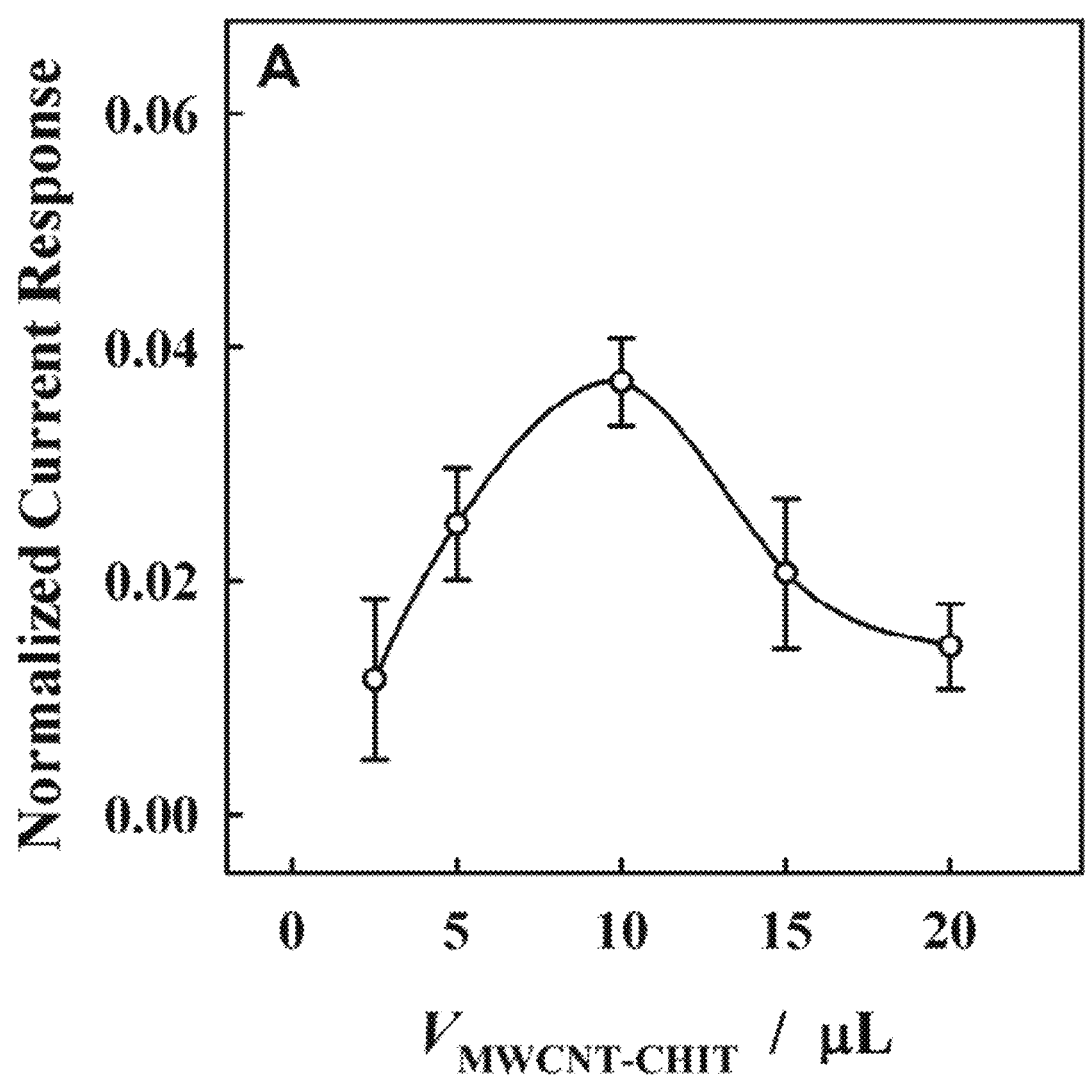
FIG. 10 is a chart depicting the effects of the added volumes of MWCNT-CHIT hybrid suspension.

The fabrication conditions of the enzyme electrodes have been optimized. FIG. 10 shows the influence of the added volume of MWCNT-CHIT hybrid suspension on the NCR of the OECTs to an addition of glucose. Three identical gate electrodes 20 are prepared for each condition. Error bar shows the standard deviation of the NCR for the three electrodes. It can be found that the volume of 10 μL corresponds to the largest NCR to an addition of 1 μM glucose. This may be due to a compromise of two factors. Firstly, a small amount of MWCNT-CHIT hybrid may not result in sufficient immobilization of GOx molecules. Secondly, too much MWCNT-CHIT hybrid on a Pt substrate may lead to a thick film at the interface and prohibit charge transfer. Therefore, a predetermined amount of MWCNT-CHIT hybrid on a Pt electrode will exhibit the maximum effect.

Figure 11:
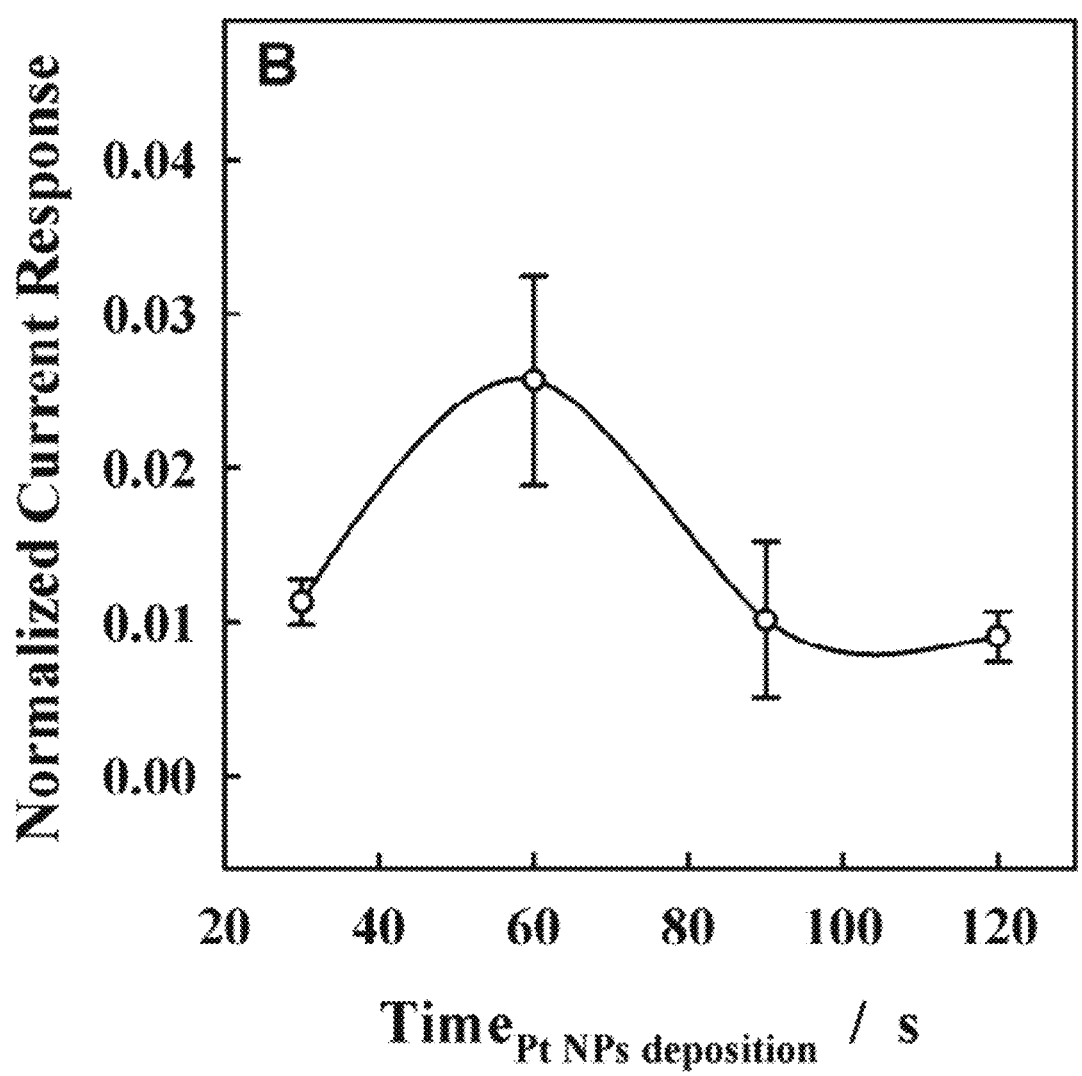
FIG. 11 is a chart depicting the Pt-NPs electro-deposition time on the Normalized Current Response using MWCNT-CHIT/GOx/Pt and CHIT/GOx/Pt-NPs/Pt gate electrodes to additions of glucose where the glucose concentration is (A), 1 µM; (B), 0.05 µM, and the applied $V_G$ is 0.4 V.

FIG. 11 shows the influence of the deposition time of Pt-NPs on the NCR of the OECTs. For each condition, three identical electrodes are prepared. The device exhibits the largest NCR when the deposition time is 60 s, which can be attributed to the optimal size and high density of Pt-NPs deposited at this condition. If the fabrication conditions of MWCNT-CHIT/GOx/Pt gate electrode 20A and CHIT/GOx/Pt-NPs/Pt gate electrode 20B are not specifically described, the electrodes 20A, 20B are prepared with the optimum conditions.

Figure 12:
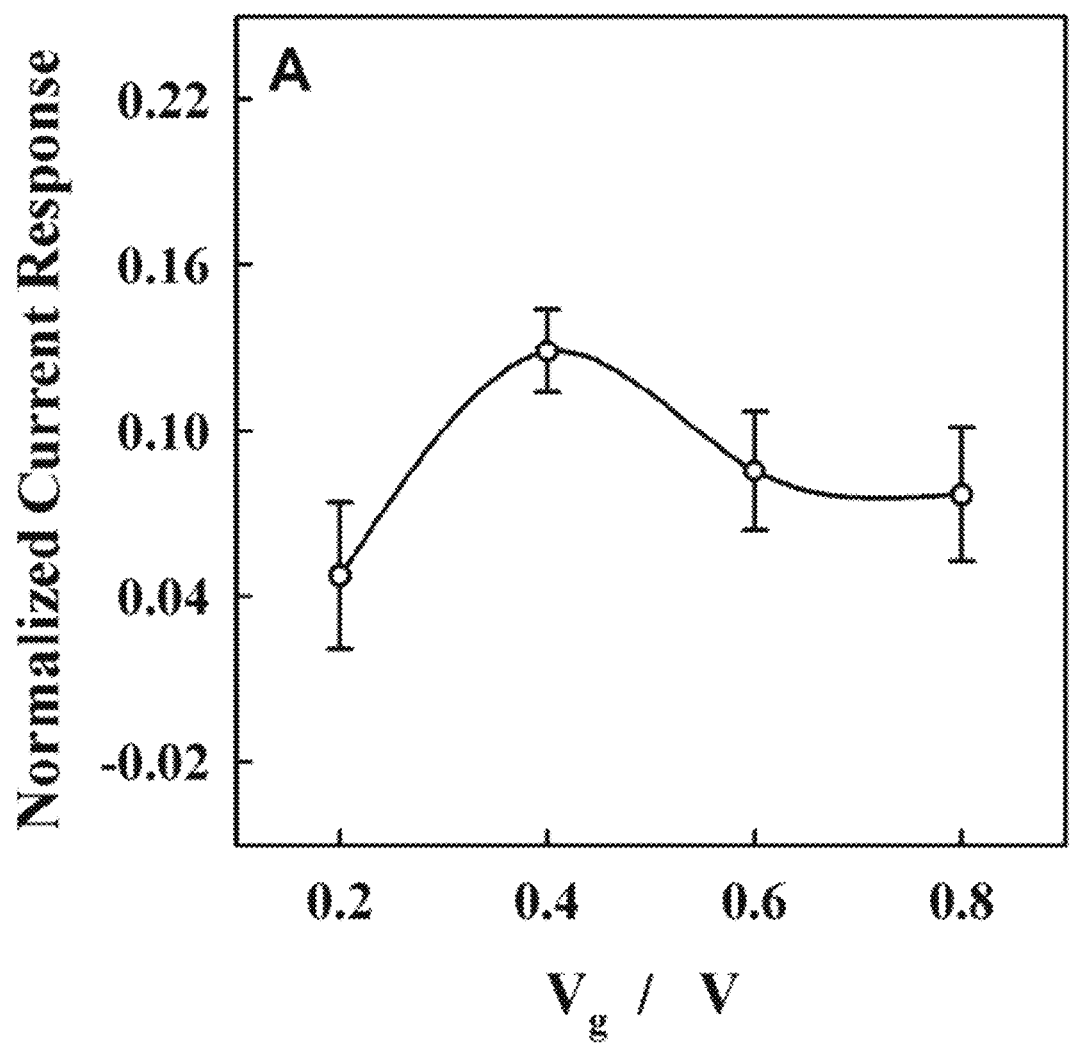
FIG. 12 is a chart depicting the effects of the applied gate voltage ($V_G$) on the Normalized Current Response using MWCNT-CHIT/GOx/Pt (A) and CHIT/GOx/Pt-NPs/Pt (B) gate electrodes to additions of glucose with a glucose concentration of 100 µM.
Figure 13:
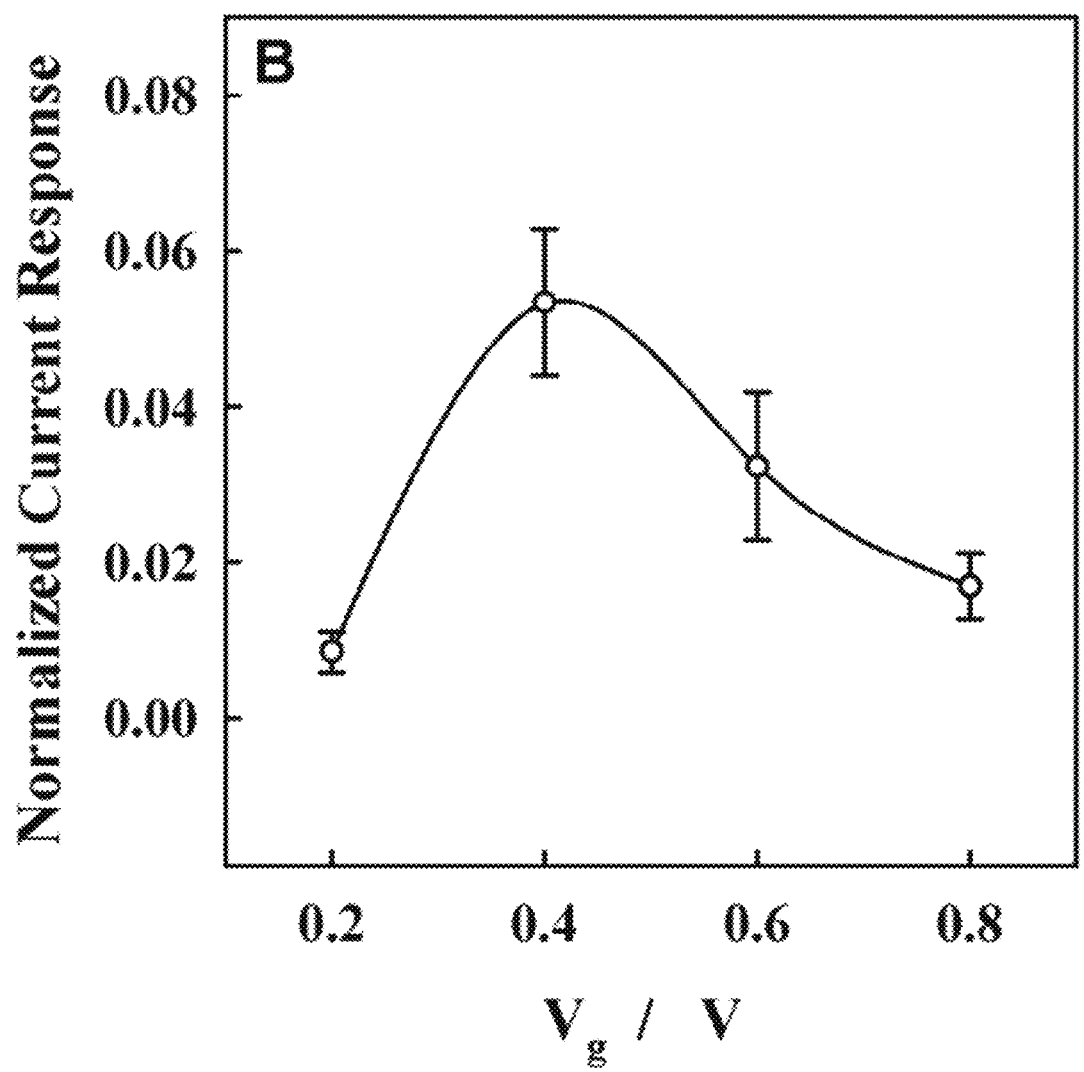
FIG. 13 is a is a chart depicting the effects of the applied gate voltage ($V_G$) on the Normalized Current Response using MWCNT-CHIT/GOx/Pt (A) and CHIT/GOx/Pt-NPs/Pt (B) gate electrodes to additions of glucose with a glucose concentration: of 0.5 µM.

FIGS. 12 and 13 show the effect of the applied $V_G$ on the NCR of OECTs 10 to glucose by using MWCNT-CHIT/GOx/Pt gate electrode 20A and CHIT/GOx/Pt-NPs/Pt gate electrode 20B. When the applied gate voltage $V_G$ is 0.4 V, the OECTs 10 show the largest NCR for both MWCNT-CHIT/GOx/Pt gate electrode 20A and CHIT/GOx/Pt-NPs/Pt gate electrode 20B. Further increase of the applied $V_G$ results in a decrease of the NCR. Therefore, 0.4 V is selected in the experiments.

Figure 14:
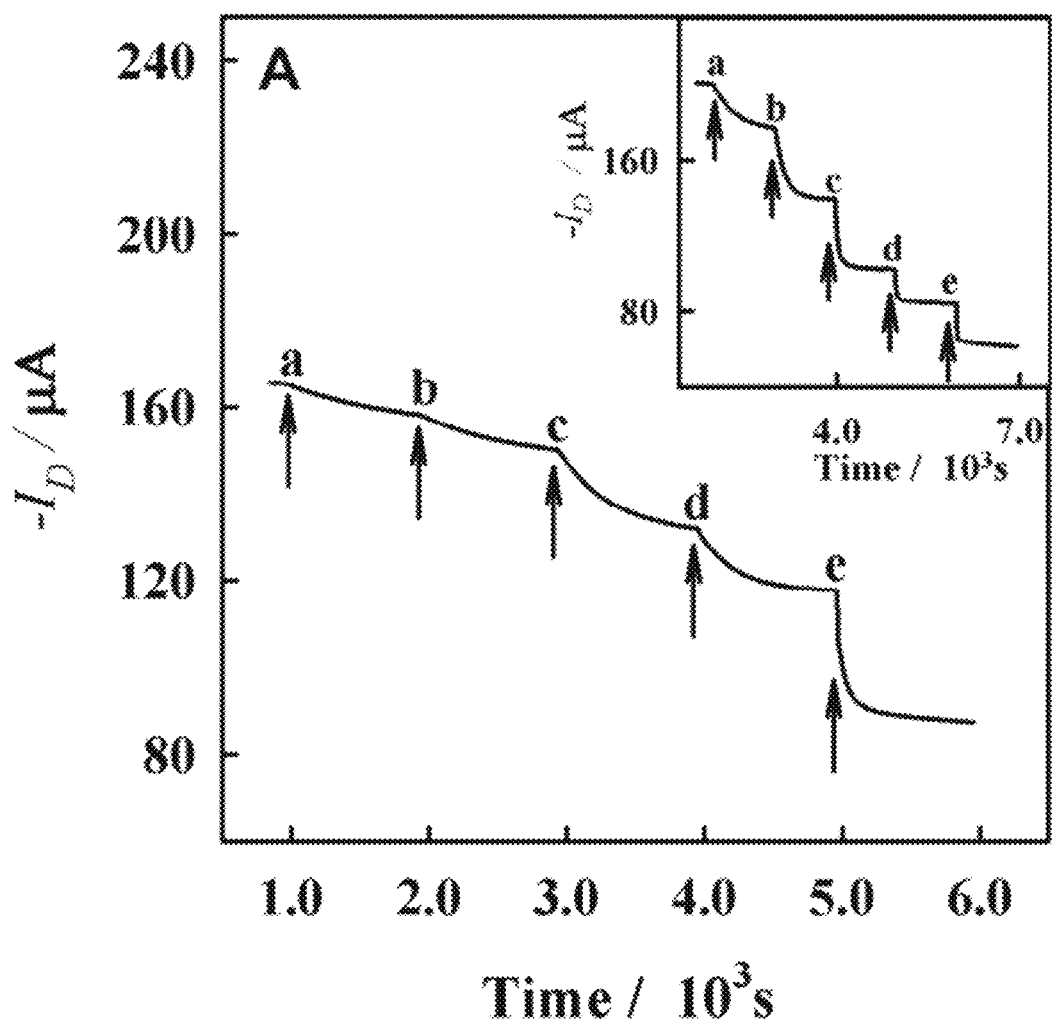
FIG. 14 is a chart depicting typical $I_D$ vs. time curves of the PEDOT:PSS device using MWCNT-CHIT/Pt, and Pt (insert plot) where Pt-NPs/Pt gate electrodes to the addition of $H_2O_2$ in PBS (pH 7.2) solutions. $V_G$ is fixed at 0.4 V. $H_2O_2$ additions: a~e: 0.1, 1, 5, 10 and 100 µM.
Figure 15:
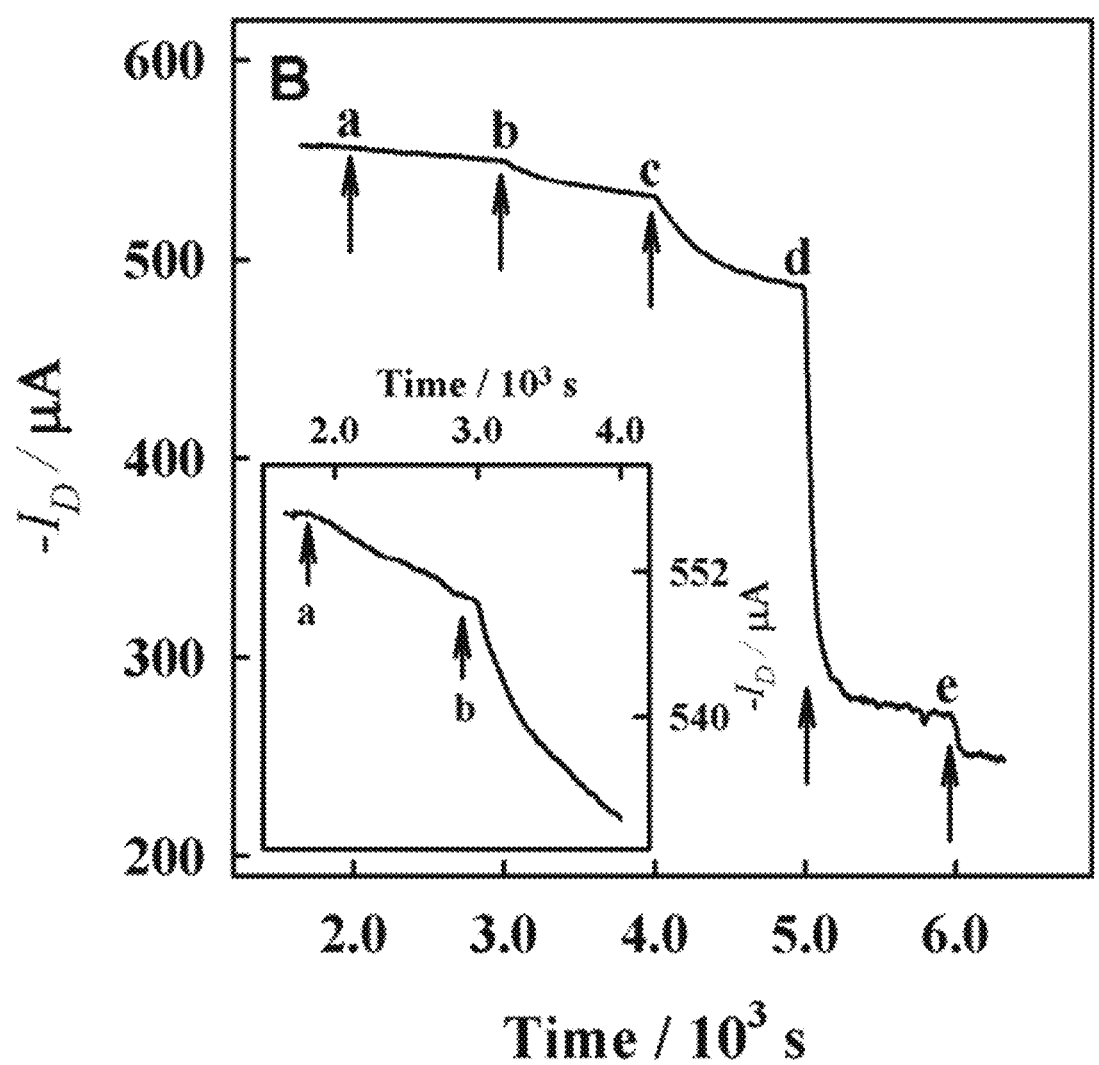
FIG. 15 is a chart depicting typical $I_D$ vs. time curves of the PEDOT:PSS device using MWCNT-CHIT/Pt, and Pt (insert plot) where Pt-NPs/Pt gate electrodes to the addition of $H_2O_2$ in PBS (pH 7.2) solutions, and $V_G$ is fixed at 0.4 V. $H_2O_2$ additions: a~e: 0.005, 0.05, 0.5, 5 and 10 µM.
Figure 16:
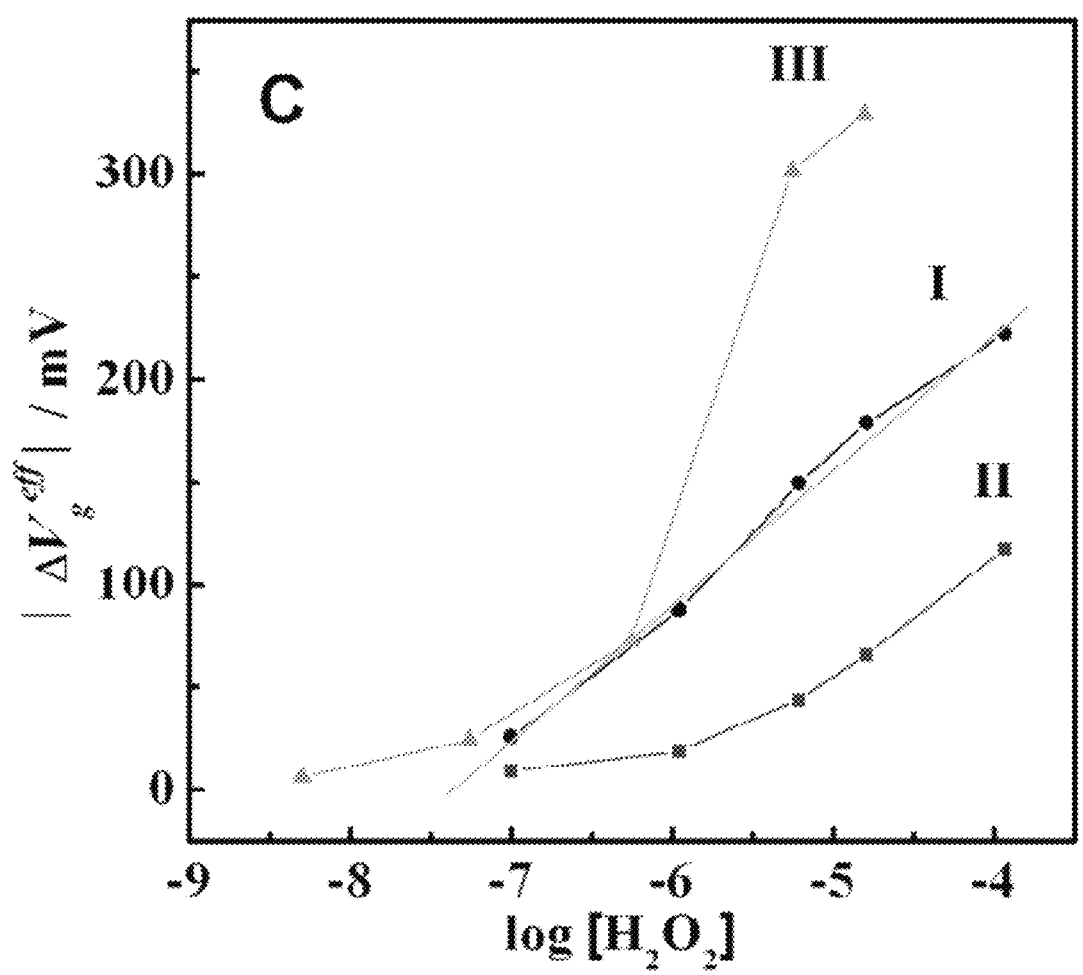
FIG. 16 is a chart depicting dependence of $\Delta V_g^{eff}$ on the concentration of log $[H_2O_2]$ for Pt (line I), MWCNT-CHIT/Pt (line II), and Pt-NPs/Pt (line III) gate electrodes.

The determination of glucose using OECT 10 is intrinsically the detection of $H_2O_2$ produced by the enzymatic reaction of GOx and glucose, and therefore the response of OECTs 10 is investigated with different gate electrodes 20 to the addition of $H_2O_2$ and the corresponding results are shown in FIGS. 14 to 16. The OECTs 10 showed obvious responses (decrease of $I_D$) to the addition of at least 0.1 μM $H_2O_2$ when MWCNT-CHIT/Pt gate electrode 20A or Pt electrode have been used as gate electrodes. Actually, the modification of MWCNT-CHIT on the Pt electrodes cannot induce any improvement on the sensitivity of the device 10 to $H_2O_2$, as shown in FIG. 14. On the contrary, the relative change in channel current $I_D$ ($\Delta I_D$) for flat Pt gate electrode is even larger than that for the MWCNT-CHIT/Pt gate electrodes 20A. Referring to FIG. 15, for Pt-NPs/Pt gate electrodes 20B, the device 10 shows an obvious response to an addition of 5 nM $H_2O_2$ (insert plot of FIG. 15), which is much better than the detection limit of the devices with MWCNT-CHIT/Pt gate electrodes or Pt gate electrodes. Therefore the modification of Pt-NPs on the surface of a Pt gate electrode can dramatically improve the sensitivity of the OECTs 10 to $H_2O_2$ due to the excellent electrocatalytic activity of the Pt-NPs.

The change of the channel current $I_D$ is induced by the modulation of effective gate voltage $V_g^{eff}$ due to the electro-oxidation of $H_2O_2$ at the gate electrode 20. Therefore the change of the effective gate voltage can be directly calculated from the change of the channel current. The dependence of $\Delta V_g^{eff}$ as a function of $H_2O_2$ concentration is shown in FIG. 16. It can be found that the OECT 10 using a Pt-NPs/Pt gate electrode 20B exhibits the lowest detection limit and the highest sensitivity to $H_2O_2$ in the three types of gate electrodes. The high sensitivity of the device with a Pt-NPs/Pt gate electrode 20B cannot be only attributed to the big surface area of the gate electrode. On the contrary, experiments show that a bigger gate electrode normally induces a lower sensitivity of the device 10.

The device with a flat Pt gate electrode shows a logarithmic relationship between the concentration of $H_2O_2$ and the shift of gate voltage $\Delta V_g^{eff}$, as described by Equation (2). The fitting curve shows that the effective gate voltage decreases by 67 meV when the concentration of $H_2O_2$ is increased by one order of magnitude, which is consistent with reported results. However, Equation (2) is not applicable in the devices 10 with nanomaterials modified on the gate electrodes 20B, which maybe due to more complicated surface morphology at the gate electrodes 20B.

The high sensitivity of the device with a Pt-NPs/Pt gate electrode 20B can be attributed to the excellent electrocatalytic activity of Pt-NPs and the amplified effects of ions near the electrodes when the diffusion layers around the Pt-NPs overlap. In this case, the ions generated at a Pt-NP will change the potential around the adjacent nanoparticles and thus the potential drop at the surface of the gate electrode 20 becomes higher, which induces a bigger change of the effective gate voltage. In FIGS. 2 to 7, the average size of the Pt-NPs is about 100 nm and the average distance between neighboring Pt-NPs is about 50 nm for the deposition time of 60 s. Both the size and the distance increase with the increase of deposition time. The thickness of double layer near a Pt electrode in PBS solution is about tens of nanometers. Therefore the average size of the Pt-NPs and the distance between neighboring Pt-NPs are critical to the amplified effect, which may be one reason for the different responses of the devices 10 with Pt-NPs deposited for different periods of time.

Figure 17:
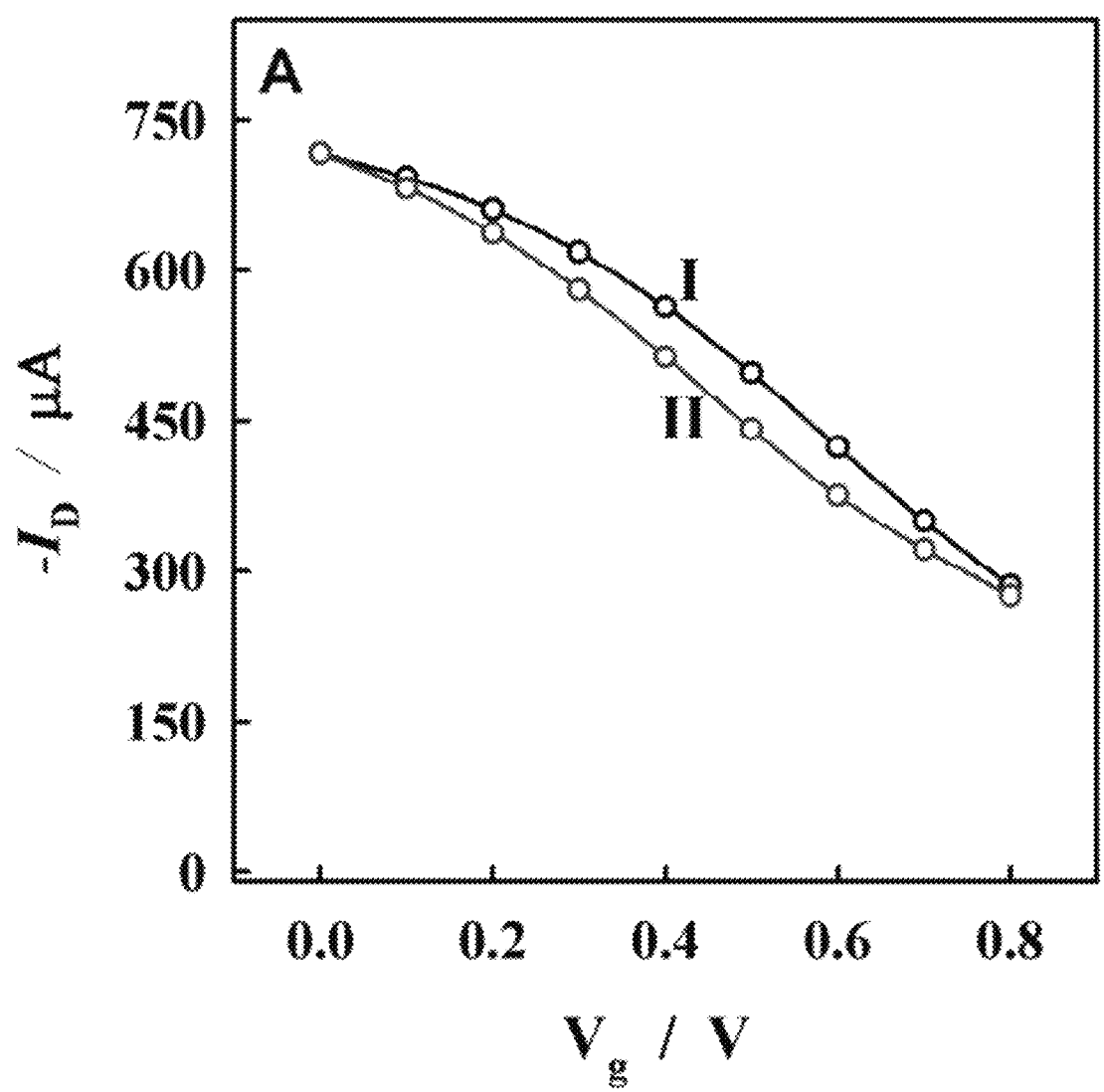
FIG. 17 is a chart depicting typical $I_D$ vs. $V_G$ curves of the PEDOT:PSS device using MWCNT-CHIT/GOx/Pt gate electrodes where the devices are characterized in blank (I) and 100 µM glucose (II) PBS (pH 7.2) solutions.
Figure 18:
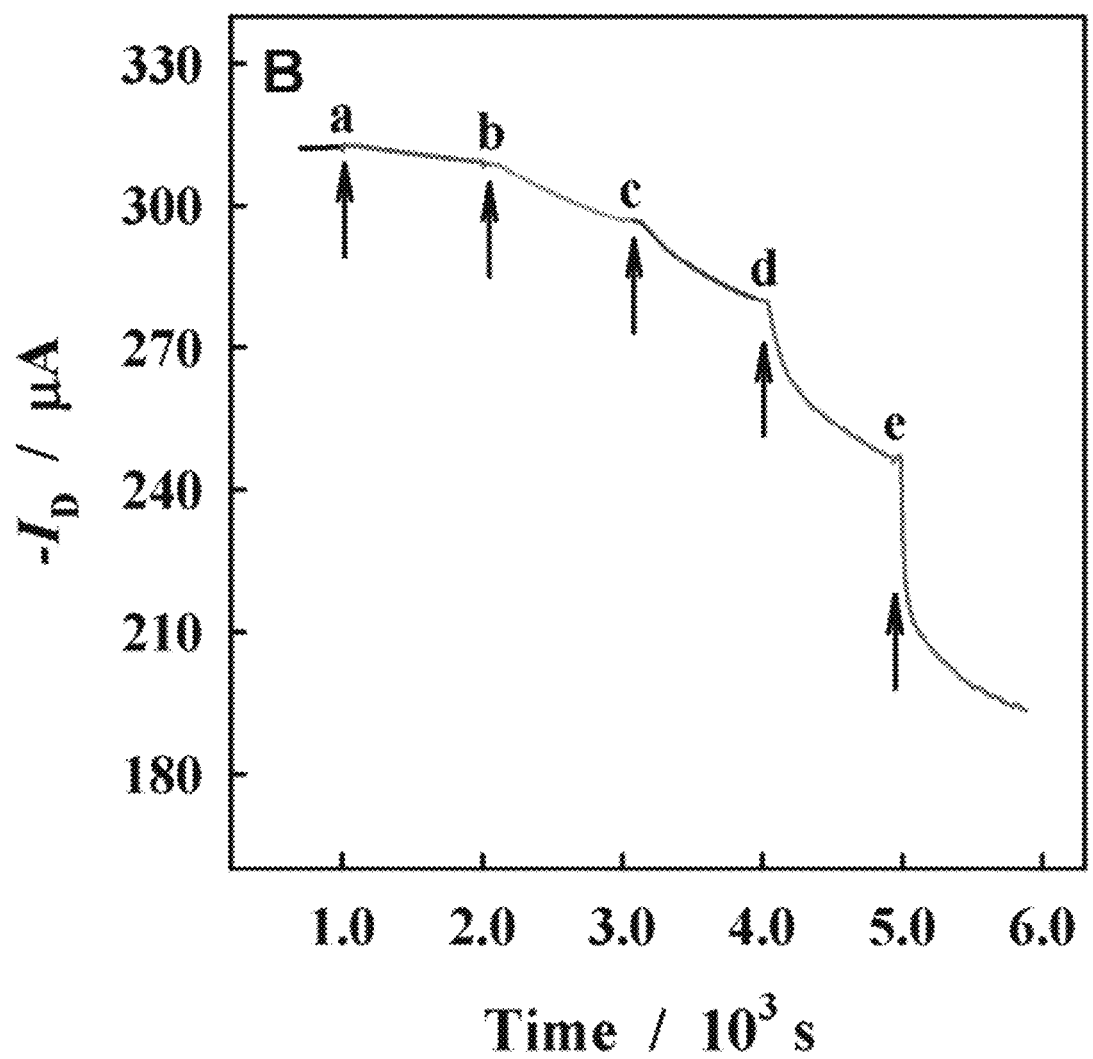
FIG. 18 is a chart depicting typical $I_D$ vs. time curves of the PEDOT:PSS device using MWCNT-CHIT/GOx/Pt gate electrodes and glucose additions, a~e: 0.5, 1, 10, 100 µM and 1 mM.
Figure 19:
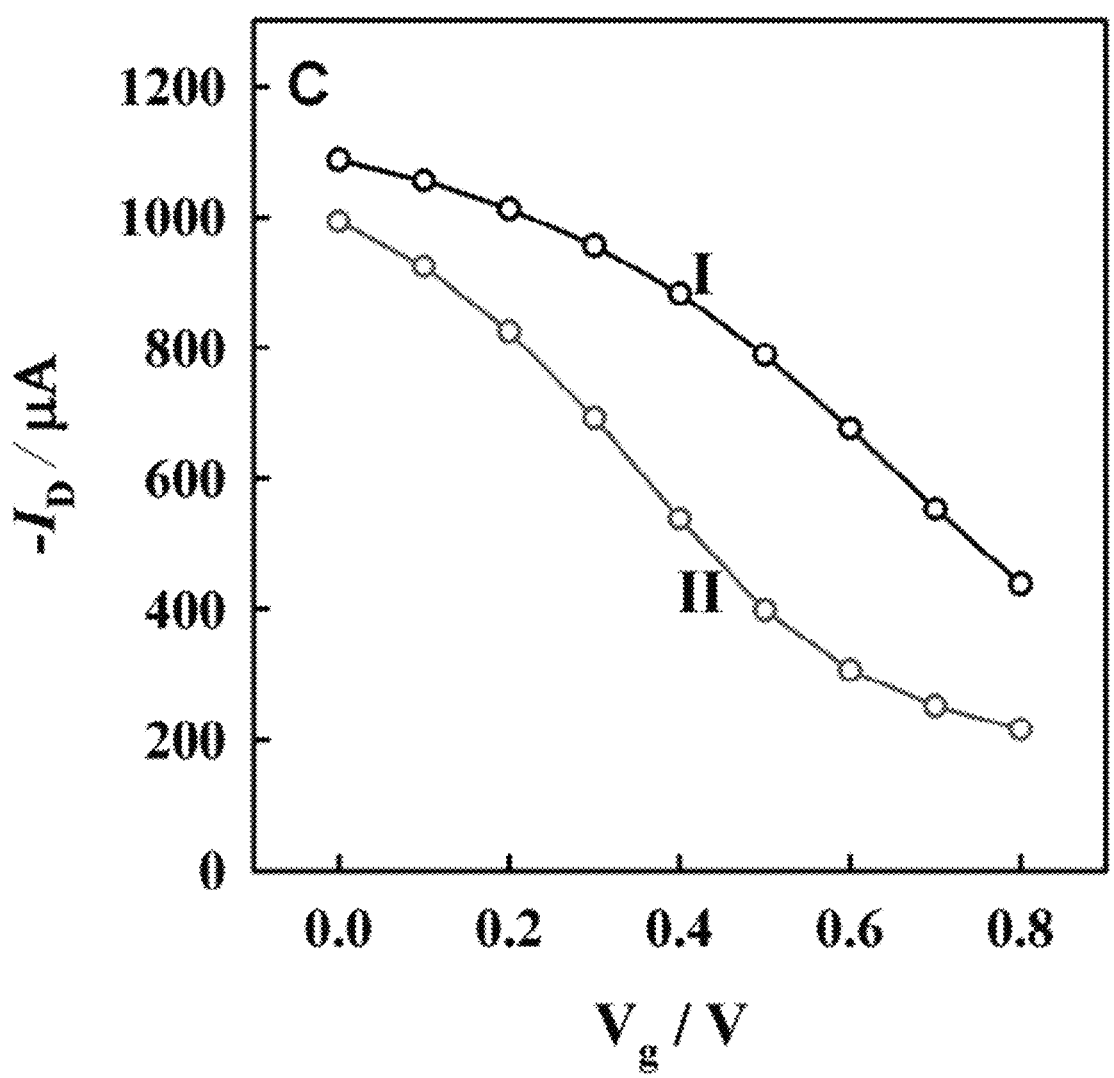
FIG. 19 is a chart depicting typical $I_D$ vs. $V_G$ curves of the PEDOT:PSS device using CHIT/GOx/Pt-NPs/Pt gate electrodes where the devices are characterized in blank (I) and 100 µM glucose (II) PBS (pH 7.2) solutions.
Figure 22:
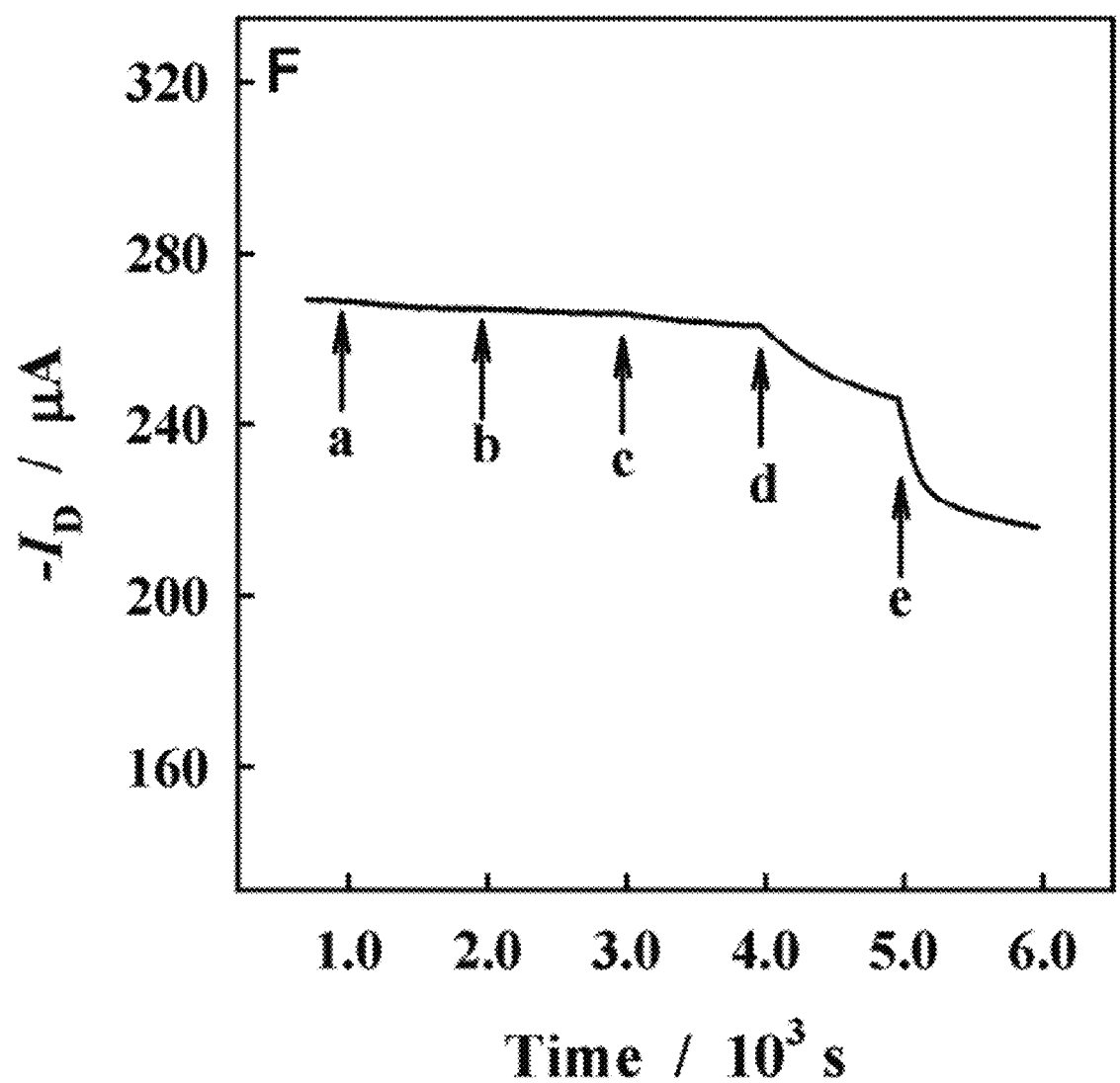
FIG. 22 is a chart depicting typical $I_D$ vs. time curves of the PEDOT:PSS device using CHIT/GOx/Pt gate electrodes and glucose additions, a~e: 0.5, 1, 10, 100 µM and 1 mM.

Next, the three types of gate electrodes 20 are modified with GOx and used for glucose sensing. FIGS. 17 to 22 shows the current responses of OECTs 10 with different gate electrodes to additions of glucose. Referring to FIG. 17, for a MWCNT-CHIT/GOx/Pt gate electrode 20A, an addition of glucose led to a horizontal shift of the transfer characteristic of the OECT 10 to the left, which can be attributed to the increase of the effective gate voltage due to the increase of $[H_2O_2]$. Referring to FIG. 18, the current change can be observed more clearly when the device was characterized at a constant gate voltage. The OECT 10 with a MWCNT-CHIT/GOx/Pt gate electrode 20A shows an obvious response ($\Delta I_D$ is about 3.8 μA) to an addition of 0.5 μM glucose. Referring to FIG. 22, however, the device 10 with a CHIT/GOx/Pt gate electrode 20B shows no change of $I_D$ until 10 μM glucose is added. These results suggest that the surface modification of Pt electrodes with a MWCNT-CHIT hybrid can improve the sensitivity of the OECTs 10 to glucose, which can be attributed to the large active surface area of a MWCNT-CHIT hybrid for GOx immobilization and its good biocompatibility in keeping enzymatic bioactivity.

Figure 20:
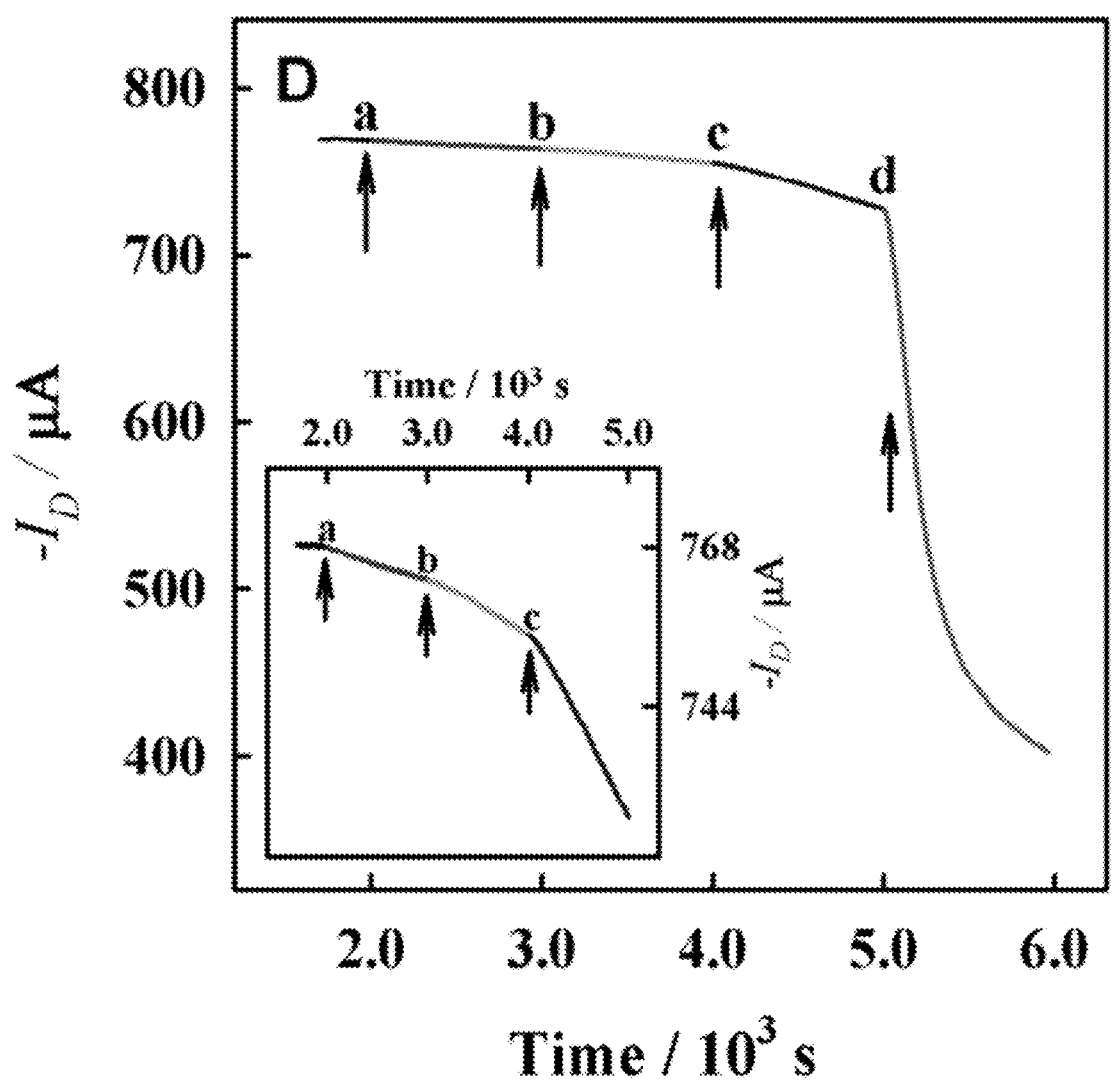
FIG. 20 is a chart depicting typical $I_D$ vs. time curves of the PEDOT:PSS device using CHIT/GOx/Pt-NPs/Pt gate electrodes and glucose additions: a~d: 0.005, 0.05, 0.5, and 5 µM.
Figure 21:
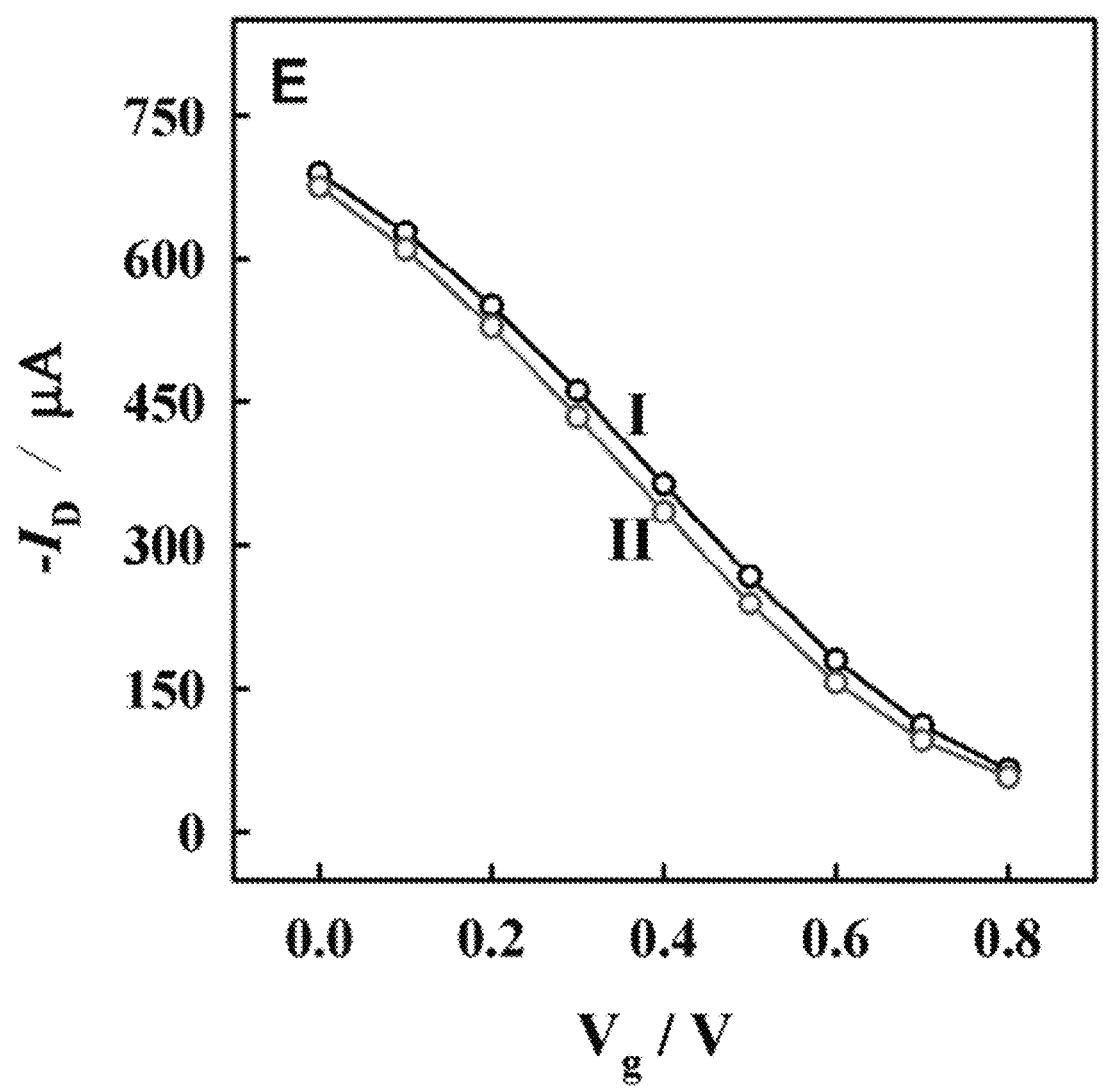
FIG. 21 is a chart depicting typical $I_D$ vs. $V_G$ curves of the PEDOT:PSS device using CHIT/GOx/Pt gate electrodes where the devices are characterized in blank (I) and 100 µM glucose (II) PBS (pH 7.2) solutions.

Referring to FIG. 20, the device 10 with a CHIT/GOx/Pt-NPs/Pt gate electrode 20B exhibits a pronounced response to an addition of 5 nM glucose, which is much more sensitive than the device using a MWCNT-CHIT/GOx/Pt gate electrode 20A. These results are reasonable because the device with a Pt-NPs/Pt electrode shows a much better detection limit to $H_2O_2$ than that of the device with a MWCNT-CHIT/Pt gate electrode 20A. In addition, the big surface area of Pt-NPs will enable more efficient enzyme immobilization on the gate electrode than a flat Pt electrode. Therefore the lowest detection limit and the highest sensitivity to glucose realized by using a CHIT/GOx/Pt-NPs/Pt gate electrode 20B can be attributed to the high sensitivity to $H_2O_2$, large surface area for GOx immobilization and good biocompatibility of the Pt-NPs.

Figure 23:
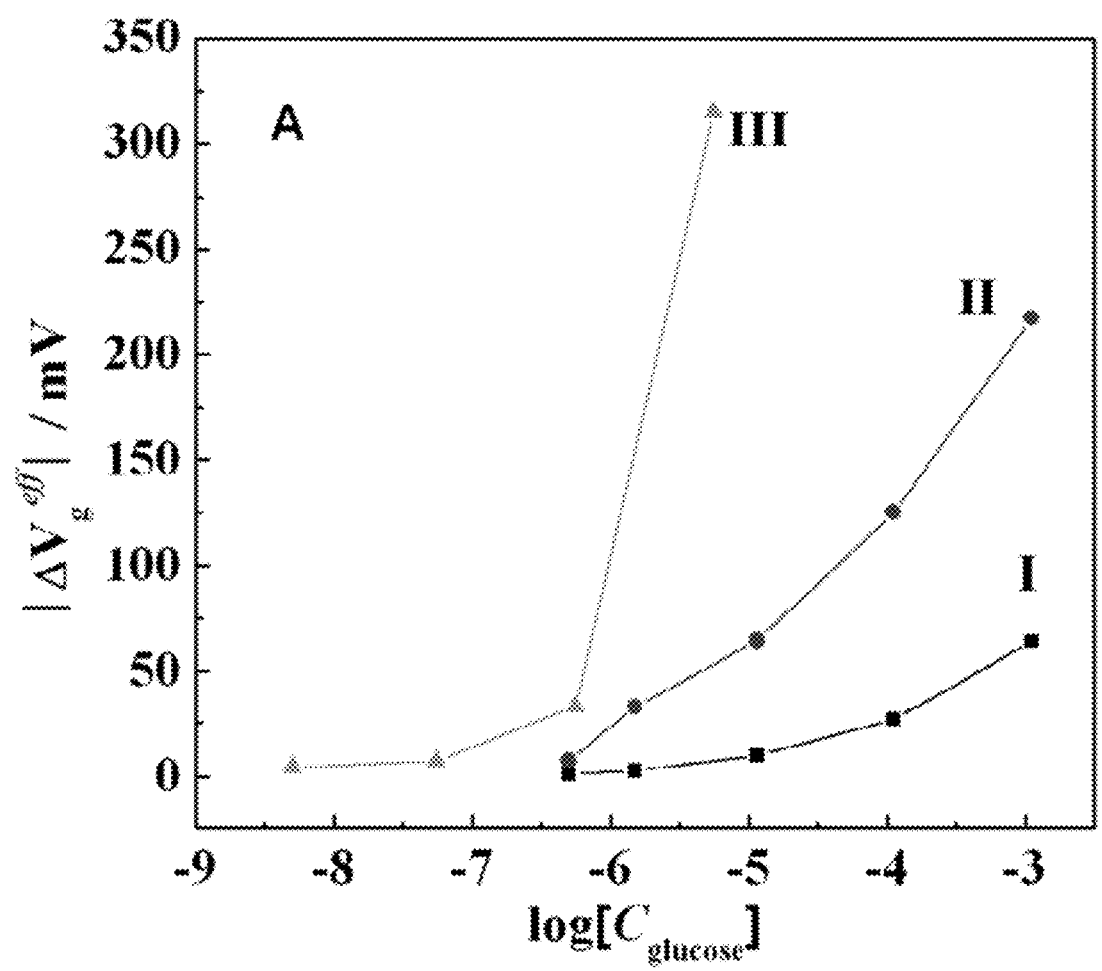
FIG. 23 is a chart depicting the dependence of $\Delta V_g^{eff}$ and Normalized Current Response for CHIT/GOx/Pt (line I), MWCNT-CHIT/GOx/Pt (line II) and CHIT/GOx/Pt-NPs/Pt (line III) gate electrodes.
Figure 24:
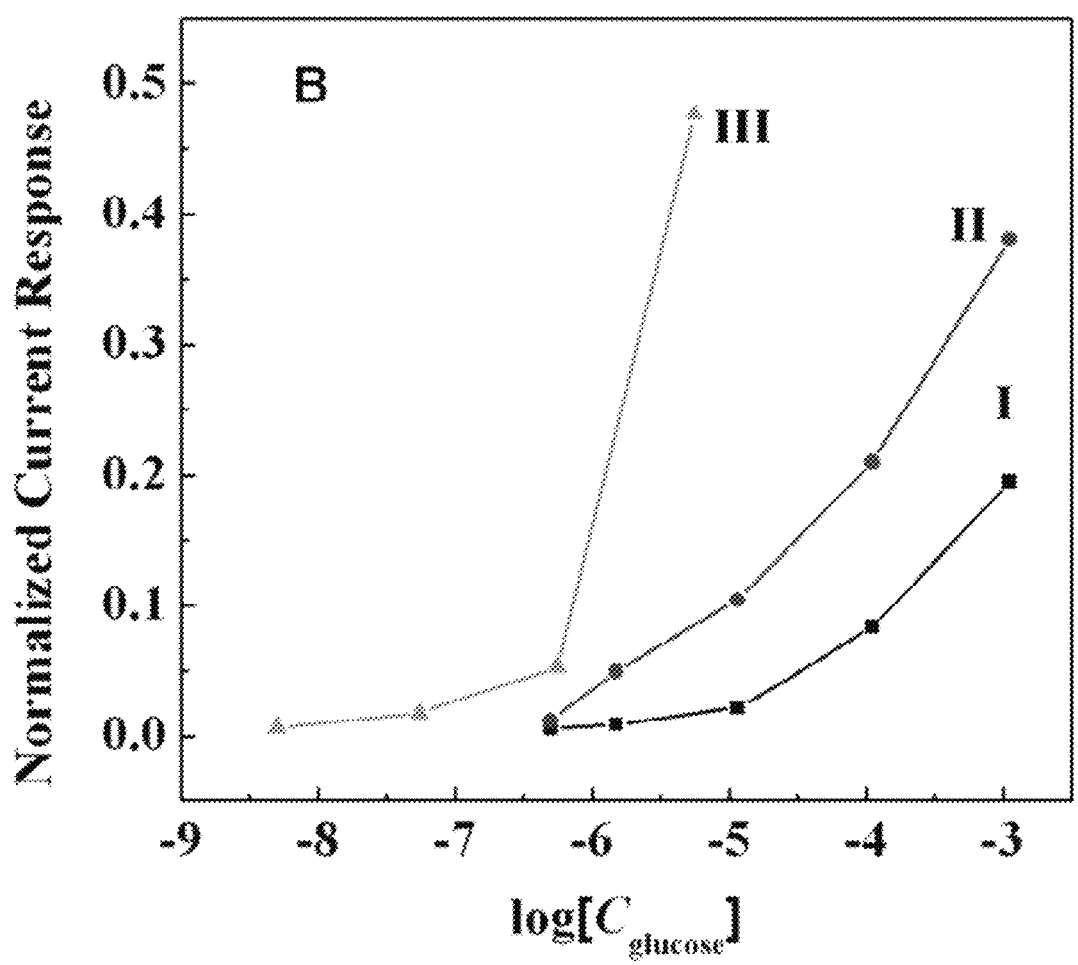
FIG. 24 is a chart depicting the dependence of $\Delta V_g^{eff}$ as functions of log $[C_{glucose}]$ for CHIT/GOx/Pt (line I), MWCNT-CHIT/GOx/Pt (line II) and CHIT/GOx/Pt-NPs/Pt (line III) gate electrodes.

FIGS. 23 and 24 show the dependence of $\Delta V_g^{eff}$ and normalized current response (NCR) as a function of glucose concentration by using various gate electrodes. Nonlinear relationships can be found for all of the devices. The OECT 10 using a CHIT/GOx/Pt-NPs/Pt gate electrode 20B exhibits the largest $\Delta V_g^{eff}$ and NCR (line III) amongst these three devices.

Figure 25:
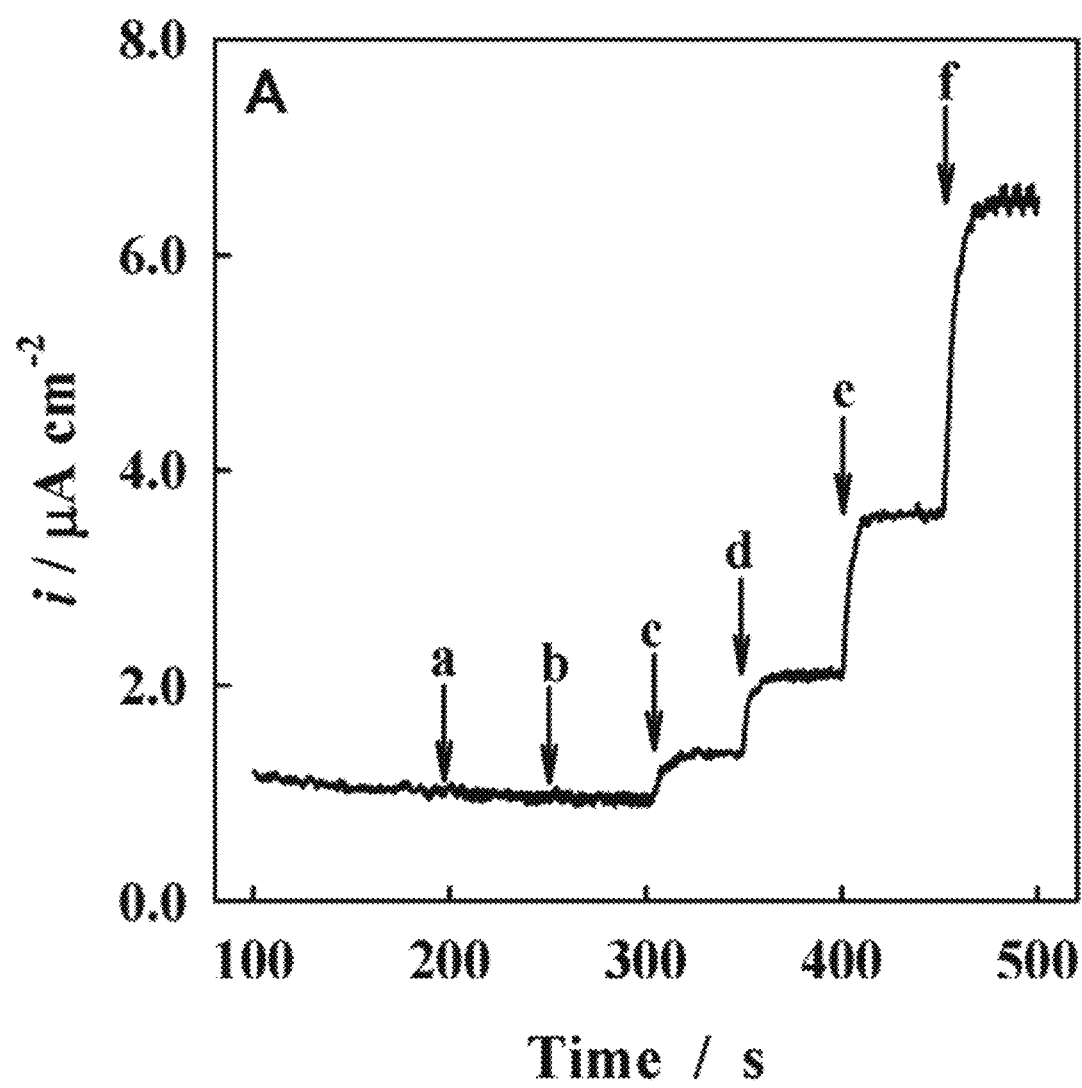
FIG. 25 is a chart depicting amperometric responses of the MWCNT-CHIT/GOx/Pt electrodes to additions of glucose with glucose additions: a~f: 1, 10, 20, 40, 100 and 200 µM, and the applied potential is 0.4 V vs. Ag/AgCl.
Figure 26:
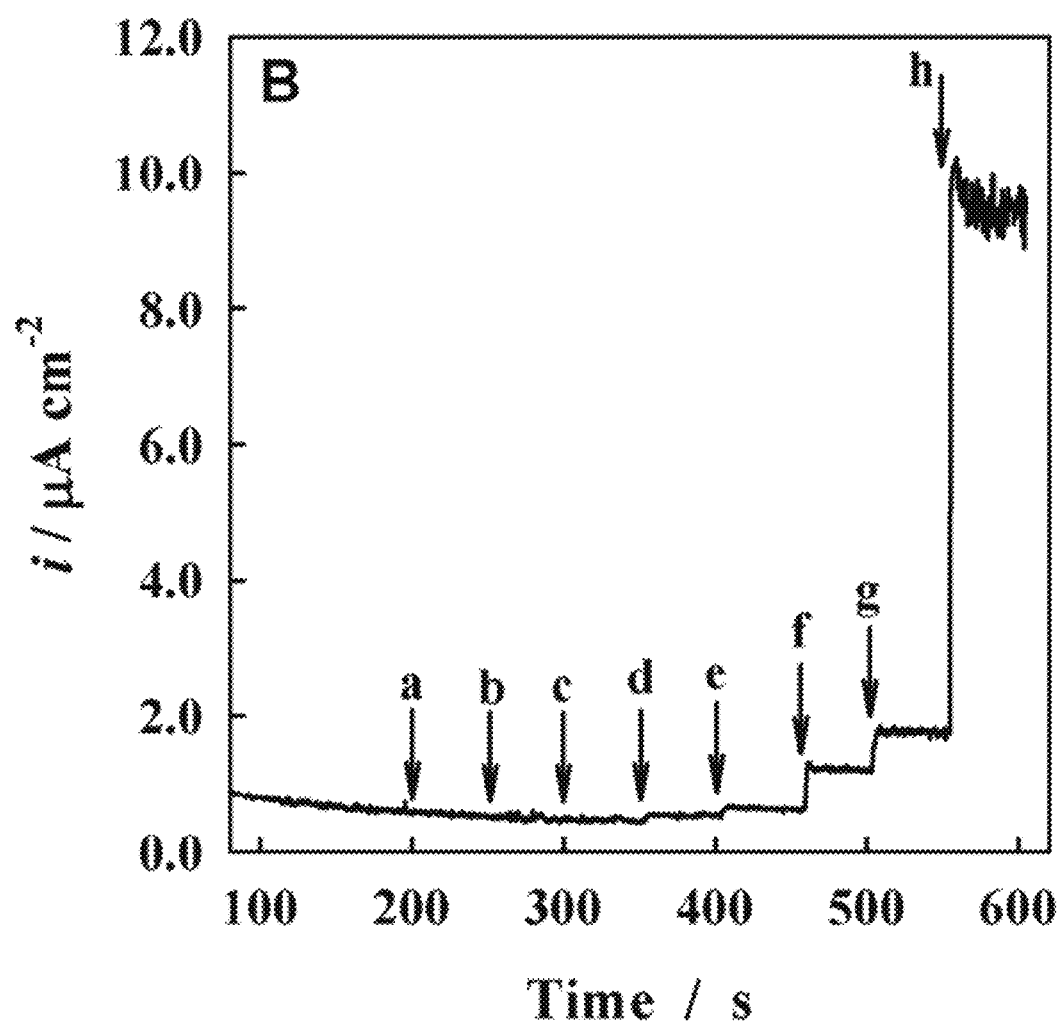
FIG. 26 is a chart depicting amperometric responses of the CHIT/GOx/Pt-NPs/Pt (B) electrodes to additions of glucose with glucose additions: a~h: 0.005, 0.05, 0.5, 5, 10, 100, 100, and 500 µM, and the applied potential is 0.4 V vs. Ag/AgCl.

The responses of the three gate electrodes 20 to additions of glucose are also characterized with electrochemical amperometric method for comparison. As shown in FIGS. 25 and 26, the detection limits of the MWCNT-CHIT/GOx/Pt gate electrode 20A and CHIT/GOx/Pt-NPs/Pt gate electrode 20B to glucose are 20 µM and 5 µM, respectively, which are much higher than the detection limits of OECTs 10 with the two electrodes. Therefore the sensors based on OECTs 10 are much more sensitive for glucose sensing than a typical electrochemical amperometric detection. In addition, the detection limit of the OECT 10 with a CHIT/GOx/Pt-NPs/Pt gate electrode 20B is much better than those of the electrochemical detections with GOx/Pt-NPs modified electrodes reported in some literatures (0.5 µM).

For a transistor-based sensor, the device is actually sensitive to the modulations of gate voltage at interfaces due to the effect of analyte. A small change in the gate voltage of a transistor can result in a big variation in the channel current. Therefore an OECT-based biosensor is a combination of a sensor and an amplifier, which can show much higher sensitivity than traditional techniques.

The device with a CHIT/GOx/Pt-NPs/Pt gate electrode 20B shows an excellent selectivity to glucose. The addition of 0.5 µM ascorbic acid or uric acid cannot induce any change of the channel current at the gate voltage of 0.4V. Since the device 10 shows the detection limit down to 5 nM to glucose, the interference of the ascorbic acid and uric acid is negligible. The excellent selectivity to glucose can be attributed to the GOx immobilized on the gate electrode 20B and the different electrocatalytic activity of Pt-NPs to different analyte.

The OECT 10 shows very stable performance when it is characterized in aqueous solutions for more than 4 days. However, the more important part of the glucose sensor is the CHIT/GOx/Pt-NPs/Pt gate electrode 20B since the device 10 is sensitive to the effective gate voltage. The stability of an OECT 10 with a CHIT/GOx/Pt-NPs/Pt gate electrode 20B is characterized for 8 days. The device 10 is measured everyday and stored in a refrigerator at 4° C. after each measurement. The responses of the device ($\Delta V_g^{eff}$) to additions of 5 nM and 1 µM glucose in PBS solutions decrease for about 30% and 20% after 8 days, respectively. The decrease of the sensitivity can be attributed to the degradation of the enzymatic activity of the immobilized GOx and the loss of GOx on the gate electrode 20B during the repetitive measurements, which are common problems for such enzyme electrodes. Since the device 10 is suitable for low-cost disposable sensing, the degradation of the device 10 will not be an important issue during real use. The device 10 is also portable and may be easily carried by users.

The performance of OECTs 10 with enzyme-modified Pt gate electrodes as glucose sensors are significantly improved when the gate electrodes 20 are modified with nanomaterials, including MWCNTs and Pt-NPs. This is because of the excellent electrocatalytic properties and large surface area of the nanomaterials. The detection limits of the OECTs 10 using a MWCNT-CHIT/GOx/Pt gate electrode 20A and CHIT/GOx/Pt-NPs/Pt gate electrode 20B reach 0.5 µM and 5 nM, respectively, which are much better than that for a device without nanomaterials (CHIT/GOx/Pt electrode, 10 µM). The OECT-based glucose sensors are much more sensitive than electrochemically amperometric detections with the same electrodes, indicating that OECTs 10 are excellent transducers for highly sensitive biosensors.

Advantageously, the sensor 10 is able to detect glucose levels in bodily fluid which are usually very low such as saliva, tissue fluid, sweat and aqueous humor. The sensor 10 has a much lower detection limit of 50 nM compared to prior art devices, also a glucose level of 0.5 µM in the bodily fluid can be detected by the sensor 10.

Also, the OECT 10 operates at low work voltages at ~1V in an aqueous environment. A small change in the gate voltage will induce a big change in the channel current of the OECT 10. Therefore, the device 10 is highly sensitive to an electromechanical reaction at the gate electrode 10 or the active layer of the channel of the OECT 10. The device 10 can be miniaturized to the size of micrometers, and can be highly integrated with other testing devices.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

We claim:

1. A non-invasive glucose sensor for detecting an amount of glucose in bodily fluid, comprising:
    an organic electrochemical transistor (OECT) having (i) a source, a drain and a transistor channel between the source and the drain and (ii) a gate electrode separated from the source, the drain, and the transistor channel, wherein the gate electrode is in ionic contact with the transistor channel through an electrolyte;
    wherein a surface of the gate electrode is modified with an enzyme and a nanomaterial to increase sensitivity and selectivity of the glucose sensor; and
    wherein the nanomaterial is any one from the group consisting of: multi-walled carbon nanotubes (MWCNTs) and platinum nanoparticles (Pt-NPs).

2. The sensor according to claim 1, wherein the gate electrode is a Pt gate electrode.

3. The sensor according to claim 1, wherein the enzyme is glucose oxidase (GOx).

4. The sensor according to claim 1, wherein the bodily fluid is any one from the group consisting of: saliva, tissue fluid, sweat and aqueous humor.

5. The sensor according to claim 1, wherein the gate electrode is composed of MWCNT-chitosan/GOx/Pt or chitosan/GOx/Pt-NPs/Pt.

6. A gate electrode for a non-invasive glucose sensor, comprising:
    a surface that is modified with an enzyme and a nanomaterial to increase sensitivity and selectivity of the gate electrode, wherein the gate electrode is configured to be in ionic contact with a transistor channel through an electrolyte; and
    wherein the nanomaterial is any one from the group consisting of: multi-walled carbon nanotubes (MWCNTs) and platinum nanoparticles (Pt-NPs).

7. The gate electrode according to claim 6, wherein the enzyme is glucose oxidase (GOx).

8. The gate electrode according to claim 6, wherein the gate electrode is composed of MWCNT-chitosan/GOx/Pt or chitosan/GOx/Pt-NPs/Pt.

9. A method for manufacturing a non-invasive glucose sensor for detecting an amount of glucose in bodily fluid, the method comprising:
   drop coating a glucose oxidase (GOx) Phosphate Buffered Saline (PBS) solution onto a surface of a gate electrode of an organic electrochemical transistor (OECT) to form a GOx/Pt gate electrode; and
   drop coating a nanomaterial chitosan (CHIT) hybrid aqueous solution onto a surface of the GOx/Pt gate electrode after the GOx PBS solution has dried on the surface of the substrate,
   wherein the nanomaterial is any one from the group consisting of: multi-walled carbon nanotubes (MW-CNTs) and platinum nanoparticles (Pt-NPs).

10. A method for detecting an amount of glucose in bodily fluid, the method comprising:
    bio-catalyzing D-glucose by glucose oxidase (GOx) to produce hydrogen peroxide (H2O2) and D-glucono-1,5-lactone;
    electro-oxidizing the produced H2O2 at a surface of a gate electrode; wherein the surface of the gate electrode is modified with any one from the group consisting of: multi-walled carbon nanotubes (MWCNTs) and platinum nanoparticles (Pt-NPs).

* * * * *